(12) United States Patent
Cooper et al.

(10) Patent No.: US 9,968,637 B2
(45) Date of Patent: May 15, 2018

(54) DOPAMINERGIC NEURONS DIFFERENTIATED FROM PLURIPOTENT STEM CELLS AND USES THEREOF

(71) Applicant: THE MCLEAN HOSPITAL CORPORATION, Belmont, MA (US)

(72) Inventors: Oliver Cooper, Jamaica Plain, MA (US); Ole Isacson, Cambridge, MA (US)

(73) Assignee: THE MCLEAN HOSPITAL CORPORATION, Belmont, MA (US)

( * ) Notice: Subject to any disclaimer, the term of this patent is extended or adjusted under 35 U.S.C. 154(b) by 0 days. days.

(21) Appl. No.: 14/718,683

(22) Filed: May 21, 2015

(65) Prior Publication Data

US 2015/0250825 A1    Sep. 10, 2015

Related U.S. Application Data

(63) Continuation of application No. 13/640,750, filed as application No. PCT/US2011/032745 on Apr. 15, 2011.

(60) Provisional application No. 61/325,232, filed on Apr. 16, 2010.

(51) Int. Cl.
*A61K 35/30* (2015.01)
*C12N 5/0793* (2010.01)

(52) U.S. Cl.
CPC ............ *A61K 35/30* (2013.01); *C12N 5/0619* (2013.01); *C12N 2500/38* (2013.01); *C12N 2501/01* (2013.01); *C12N 2501/119* (2013.01); *C12N 2501/13* (2013.01); *C12N 2501/15* (2013.01); *C12N 2501/155* (2013.01); *C12N 2501/41* (2013.01); *C12N 2501/415* (2013.01); *C12N 2506/02* (2013.01); *C12N 2506/45* (2013.01)

(58) Field of Classification Search
CPC .............................. A61K 35/30; C12N 5/0169
See application file for complete search history.

(56) References Cited

U.S. PATENT DOCUMENTS

2013/0108669 A1    5/2013 Cooper et al.

OTHER PUBLICATIONS

Bjorklund and Lindvall, Nature Neuroscience, 3(6):537-544 (2000). "Cell replacement therapies for central nervous system disorders."
Pepinsky et al. The Journal of Biological Chemistry, 273(22):14037-14045 (1998). "Identification of a palmitic acid-modified form of human sonic hedgehog."
Taylor et al., Biochemistry, 40:4359-4371 (2001). "Enhanced potency of human sonic hedgehog by hydrophobic modification."
Cooper et al. Molecular and Cellular Neuroscience 45:258-266 (2010) "Differentiation of human ES and Parkinson's Disease iPS cells into ventral midbrain dopaminergic neurons requires a high activity form of SHH, FGF8A and specific regionalization by retinoic acid."
Fasano et al. Cell Stem Cell 6:336-347 (2010) "Efficient derivation of functional floor plate tissue from human embryonic stem cells."
Kittappa et al. PLoS Biology 5(12):2875-2884 (2007) "The FOXA2 gene controls the birth and spontaneous degeneration of dopamin neurons in old age."
Lee et al. Stem Cells 28:501-512 (2010) "Foxa2 and Nurr1 synergistically yield A9 nigral dopamine nuerons from human embryonic stem cells."
Perrier et al. PNAS USA 101(34):12543-12548 (2004) "Derivation of midbrain dopamine neurons form human embryonic stem cells".
Yan et al. Stem Cells 23:781-790 (2005) "Directed differentiation of dopaminergic neuronal subtypes from human embryonic stem cells."
Zhang, SC. Brain Pathology 16(2):132-142 (2006) "Neural subtype specification from embryonic stem cells."
Sonntag et al. "Enhanced yield of neuroepithelial precursors and midbrain-like dopaminergic neurons from human embryonic stem cells using the bone morphogenic protein antagonist noggin." Stem Cells (2007) 25:411-418.
Olsen et al. "Structural basis by which alternative splicing modulates the organizer activity of FGF8 in the brain." Genes Dev (2006) 20:185-198.
Cho et al. "Highly efficient and large-scale generation of functional dopamine neurons from human embryonic stem cells. " Proc Natl Acad Sci (2008) 105:3392-3397.
Chung et al. "Cell type specific gene expression of midbrain dopaminergic neurons reveals molecules involved in their vulnerability and protection." Human Molecular Genetics (2005) 14(13):1709-25.
Erceg et al. "Human embryonic stem cell differentiation toward regional specific neural precursors." Stem Cells (2009) 27:78-87.
Ferri et al. "Foxa1 and Foxa2 regulate multiple phases of midbrain dopaminergic neuron development in a dosage-dependent manner." Development (2007) 134:2761-2769.
Hynes et al. "Induction of midbrain dopaminergic neurons by Sonic hedgehog." Neuron (1995) 15:35-44.
Isacson et al. "Toward full restoration of synaptic and terminal function of the dopaminergic system in Parkinson's disease." Annals of Neurology (2003) 53:135-148.
Joksimovic et al. "Spatiotemporally separable Shh domains in the midbrain define distinct dopaminergic progenitor pools." Proc Natl Acad Sci USA (2009) 106:19185-19190.
Jonsson et al. "Identification of transplantable dopamine neuron precursors at different stages of midbrain neurogenesis." Exp Neurol (2009) 219:341-354.

(Continued)

*Primary Examiner* — Robert C Hayes
(74) *Attorney, Agent, or Firm* — David S. Resnick; Teresa A. Ptashka; Nixon Peabody LLP

(57) ABSTRACT

The present invention provides populations of neural cells derived from pluripotent cells, and methods for making and using the same. Disclosed herein are methods for generating dopaminergic neurons in vitro using a combination of agents that cause differentiation of the pluripotent cells into dopaminergic neurons. Also disclosed are methods for treating a neurodegenerative disease in a patient by generating dopaminergic neurons in vitro, and transplanting them into the brain of the patient, such that the dopaminergic neurons are sufficient to reduce or eliminate the symptoms of the neurodegenerative disease.

8 Claims, 8 Drawing Sheets

(56) References Cited

OTHER PUBLICATIONS

Lee et al. "Evidence that FGF8 signalling from the midbrain-hindbrain junction regulates growth and polarity in the developing midbrain." Development (1997) 124:959-969.
Li et al. "Coordination of sonic hedgehog and Wnt signaling determines ventral and dorsal telencephalic neuron types from human embryonic stem cells." Development (2009) 136:4055-4063.
Lin et al. "Foxa1 and Foxa2 function both upstream of and cooperatively with Lmx1a and Lmx1b in a feedforward loop promoting mesodiencephalic dopaminergic neuron development." Dev Biol (2009) 333:386-396.
Mendez et al. "Cell type analysis of functional fetal dopamine cell suspension transplants in the striatum and substantia nigra of patients with Parkinson's disease." Brain (2005) 128:1498-1510.
Okada et al. "Retinoic acid concentration dependent acquisition of neural cell identity during in vitro differentiation of mouse embryonic stem cells. " Dev. Biol. (2004) 275:124-142.
Roy et al. "Functional engraftment of human ES cell-derived dopaminergic neurons enriched by coculture with telomerase-immortalized midbrain astrocytes." Nature Medicine (2006) 12:1259-1268.
Aguila et al., "Selection Based on FOXA2 Expression Is Not Sufficient to Enrich for Dopamine Neurons From Human Pluripotent Stem Cells", Stem Cells Translational Medicine 3(9):1032-1042 (2014).
Barker et al., "Fetal dopaminergic transplantation trials and the future of neural grafting in Parkinson's disease", Lancet Neural. 12(1):84-91 (2013).
Bjorklund et al., "Embryonic stem cells develop into functional dopaminergic neurons after transplantation in a Parkinson rat model", PNAS 99(4):2344-2349 (2002).
Brownell et al., "Combined PET/MRS brain studies show dynamic and long-term physiological changes in a primate model of Parkinson disease", Nature Medicine 4(11)1308-1312 (1998).
Brownell et al., "In Vivo PET Imaging in Rat of Dopamine Terminals Reveals Functional Neural Transplants", Ann. Neurol. 43(3)387-390 (1998).
Deleidi et al., "Development of histocompatible primate-induced pluripotent stem cells for neural transplantation", Stem Cells 29(7):1052-1063 (2011).
Emborg et al., "Induced Pluripotent Stem Cell-Derived Neural Cells Survive and Mature in the Nonhuman Primate Brain", Cell Rep. 3(3):646-650 (2013).
Grealish et al., "Human ESC-Derived Dopamine Neurons Show Similar Preclinical Efficacy and Potency to Fetal Neurons when Grafted in a Rat Model of Parkinson's Disease", Cell Stem Cell 15(5):653-665 (2014).
Grealish et al., "The A9 dopamine neuron component in grafts of ventral mesencephalon is an important determinant for recovery of motor function in a rat model of Parkinson's disease", Brain 133(Pt2):482-495 (2010).
Hantraye et al., "Dopamine fiber detection by [11C]-CFT and PET in a primate model of parkinsonism", NeuroReport 3(3):265-268 (1992).

Hallett et al., "Long-term dopamine transporter expression and normal cellular distribution of mitochondria in dopaminergic neuron transplants in Parkinson's disease patients", Cell Rep. 7(6)1755-1761 (2014).
Hallett et al., "Successful function of autologous iPSC-derived dopamine neurons following transplantation in a non-human primate model of Parkinson's disease", Cell Stem Cell 16(3):269-274 (2015).
Hargus et al., "Differentiated Parkinson patient-derived induced pluripotent stem cells grow in the adult rodent brain and reduce motor asymmetry in Parkinsonian rats", PNAS 107(36):15921-15926 (2010).
Jenkins et al., "Mapping Dopamine Function in Primates Using Pharmacologic Magnetic Resonance Imaging", J. Neurosci. 24(43):9553-9560 (2004).
Kefalopoulou et al., "Long-term Clinical Outcome of Fetal Cell Transplantation for Parkinson Disease: Two Case Reports", JAMA Neurol. 71(1):83-87 (2014).
Kikuchi et al., "Survival of Human Induced Pluripotent Stem Cell-Derived Midbrain Dopaminergic Neurons in the Brain of a Primate Model of Parkinson's Disease", Journal of Parkinson's Disease 1(4):395-412 (2011).
Mendez et al., "Dopamine neurons implanted into people with Parkinson's disease survive without pathology for 14 years", Nat Med. 14(5):507-509 (2008).
Morizane et al., "Neural Induction with a Dopaminergic Phenotype from Human Pluripotent Stem Cells Through a Feeder-Free Floating Aggregation Culture", Methods in Molecular Biology 1018:11-19 (2013).
Politis et al., "Serotonergic Neurons Mediate Dyskinesia Side Effects in Parkinson's Patients with Neural Transplants", Science Translational Medicine 2(38):38ra46 (2010).
Redmond et al., "Influence of cell preparation and target location on the behavioral recovery after striatal transplantation of fetal dopaminergic neurons in a primate model of Parkinson's disease", Neurobiol Dis. 29(1):103-116 (2008).
Sanchez-Pernaute et al., "Long-Term Survival of Dopamine Neurons Derived from Parthenogenetic Primate Embryonic Stem Cells (Cyno-1) After Transplantation", Stem Cells 23(7):914-922 (2005).
Sundberg et al., "Improved cell therapy protocols for Parkinson's disease based on differentiation efficiency and safety of hESC-, hiPSC-, and non-human primate iPSC-derived dopaminergic neurons", Stem Cells 31(8):1548-1562 (2013).
Vinuela et al., "Implanted reuptake-deficient or wild-type dopaminergic neurons improve ON L-dopa dyskinesias without OFF-dyskinesias in a rat model of Parkinson's disease", Brain 131(Pt 12):3361-3379 (2008).
Wernig et al., "Neurons derived from reprogrammed fibroblasts functionally integrate into the fetal brain and improve symptoms of rats with Parkinson's disease", PNAS 105(15):5856-5861 (2008).
Wullner et al., "Dopamine Terminal Loss and Onset of Motor Symptoms in MPTP-Treated Monkeys: A Positron Emission Tomography Study with 11C-CFT", Experimental Neurology 126(2):305-309 (1994).
Tomishima, "Midbrain dopamine neurons from hESCs", in Stem Cell Book, 1-4 (2012).

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtgtctgccc acctcttctc                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcagtctgtg gggtcgtatt                                                   20

<210> SEQ ID NO 3
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 3
agaggacgac gttcactcg                                                    19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggggtgcagc aagtccatac                                                   20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtcaatcag aaggagacgg a                                                 21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgttcccata aggggatgc                                                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tatgttcgcc tgggagattc                                                   20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaaaggctgc tgaactttgg                                                   20

<210> SEQ ID NO 9
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 9
ctcgctgctg gtatgctcg                                                    19

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atcgctcgga gtttctggag a                                                 21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atggaggaga acttccaaag c                                                 21

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cccgctcctt ctcatagt                                                     18

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctcgcctttg ccgatcc                                                      17

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccttgcacat gccggag                                                      17
```

DOPAMINERGIC NEURONS DIFFERENTIATED FROM PLURIPOTENT STEM CELLS AND USES THEREOF

CROSS-REFERENCE TO RELATED APPLICATIONS

This application is a Continuation Application of U.S. application Ser. No. 13/640,750, filed Jan. 8, 2013, which is a 35 U.S.C. § 371 National Phase Entry Application of International Application No. PCT/US2011/032745 filed Apr. 15, 2011, which designates the U.S., and which claims benefit under 35 U.S.C. § 119(e) of U.S. Provisional Application No. 61/325,232, filed Apr. 16, 2010, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Dec. 12, 2012, is named 20121213_SequenceListing-TextFile_063476_073732_US and is 3,536 bytes in size.

STATEMENT OF GOVERNMENT SUPPORT

This invention was made with Government support under Grant Nos. NS039793 awarded by the National Institutes of Health and W81XWH-05-1-0555 awarded by the U.S. Department of the Army. The Government has certain rights in this invention.

FIELD OF THE INVENTION

This invention relates to the field of neural cells. Specifically, the invention provides methods for inducing pluripotent cells to differentiate into neuronal phenotypes.

BACKGROUND OF THE INVENTION

The following description is provided to assist the understanding of the reader. None of the information provided or references cited is admitted to be prior art to the present invention.

Neurodegenerative disorders such as Parkinson's, Alzheimer's, and Huntington's disease are becoming ever more prominent in our society. Parkinson's disease (PD) is a progressive neurodegenerative disease characterized clinically by bradykinesia, rigidity, and resting tremor. The motor abnormalities are associated with a specific loss of dopaminergic neurons in the substantia nigra pars compacta (SN) and depletion of striatal dopamine (DA) levels. While the loss of striatal DA correlates with the severity of clinical disability, clinical manifestations of PD are not apparent until about 80-85% of SN neurons have degenerated and striatal DA levels are depleted by about 60-80%.

DA neurons in the ventral midbrain consist of two main groups: the A9 group in the SN, and the A10 group in the medial and ventral tegmentum. Each of these cell groups project to different anatomical structures and is involved in distinct functions. A9 cells mainly project to the dorsolateral striatum, and are involved in the control of motor functions, whereas A10 cells provide connections to the ventromedial striatum, limbic and cortical regions, and are involved in reward and emotional behavior. In addition to the distinct axonal projections and differences in synaptic connectivity, these groups of DA cells exhibit differences in neurochemistry and electrophysiological properties, illustrating functional differences despite similar neurotransmitter identity. These differences in A9 and A10 cells are also reflected in their specific responses to neurodegeneration in PD. Post-mortem analyses in human PD brains demonstrate a selective cell loss of the A9 group with a survival rate of about 10% whereas the A10 group is largely spared with a survival rate of about 60%. This indicates that A9 cells are more vulnerable to intrinsic and/or extrinsic factors causing degeneration in PD. In addition, three regional gradients of neurodegeneration in the dorso-ventral/rostro-caudal/medio-lateral axis have been reported in PD. Caudally and laterally located ventral DA cells within A9 subgroups are the most vulnerable cells in PD. In contrast, the medial and rostral part of DA cell subgroups within A10 cells (i.e. rostral linear nucleus, RLi) are the least affected (5-25% cell loss).

Cell transplantation therapies have been used to treat neurodegenerative disease, including Parkinson's disease, with moderate success (e.g., Bjorklund et al., Nat. Neurosci., 3:537-544, 2000). However, wide-spread application of cell-based therapies will depend upon the availability of sufficient amounts of neuronal cells.

SUMMARY OF THE INVENTION

The present invention is based on the discovery, isolation, and characterization of specific neuronal cell populations that are derived in vitro from pluripotent cells, including embryonic stem cells (ESCs) and induced pluripotent stem (iPS) cells. The inventive cells are neurons that have the phenotype of dopaminergic neurons and are capable of structurally and functionally integrating into the host brain following transplantation. Accordingly, these cells are useful in cell replacement/transplantation therapies, including therapies designed to treat Parkinson's disease and other conditions caused by a loss of dopaminergic neurons.

In one aspect, the present invention provides a substantially homogenous population of cells derived from pluripotent stem cells contacted with an effective amount of retinoic acid, human sonic hedgehog (SHH) protein, and FGF8A protein, wherein the cells have the phenotype of SN-A9 dopaminergic neurons. Optionally, the pluripotent stem cells are further contacted with a WNT1 protein. In some embodiments, the cells are characterized as having a FOXA2$^+$ phenotype, a β-tubulin$^+$ phenotype, and/or expressing tyrosine hydroxylase.

In some embodiments, the pluripotent stem cells are human embryonic stem cells or induced pluripotent stem cells. In a particular embodiment, the induced pluripotent stem cells are Parkinson's disease (PD) patient-specific induced pluripotent stem cells.

In one aspect, the present invention provides a therapeutic composition comprising a substantially homogenous population of cells derived from pluripotent stem cells contacted with an effective amount of retinoic acid, human sonic hedgehog (SHH) protein, and FGF8A protein, wherein the cells have the phenotype of SN-A9 dopaminergic neurons, wherein the cell population is in an amount sufficient to treat a disease or condition. Optionally, the pluripotent stem cells are further contacted with a WNT1 protein. In one embodiment, the population of cells is suspended in a physiologically acceptable carrier. In one embodiment, the physiologically acceptable carrier is artificial cerebrospinal fluid. In one embodiment, the population of cells is encapsulated. In one embodiment, the population of cells is contained within an inert biomatrix.

In another aspect, the present invention provides a method for treating a disease in a subject, comprising administering to the subject a therapeutic composition comprising a substantially homogenous population of cells derived from pluripotent stem cells contacted with an effective amount of retinoic acid, human sonic hedgehog (SHH) protein, and FGF8A protein, wherein the cells have the phenotype of SN-A9 dopaminergic neurons, wherein the cell population is in an amount sufficient to treat the disease or condition. Optionally, the pluripotent stem cells are further contacted with a WNT1 protein. In one embodiment, the disease is a neurodegenerative disease. In a particular embodiment, the neurodegenerative disease is Parkinson's disease. In some embodiments, the administering comprises transplanting the dopaminergic neurons into the brain of the subject. In one embodiment, the therapeutic composition is injected into the striatum of the subject. In one embodiment, the therapeutic composition is injected into the midbrain of the subject.

In another aspect, the present invention provides a method for generating SN-A9 dopaminergic neurons, the method comprising: (a) contacting pluripotent stem cells with an effective amount of retinoic acid to form neural progenitor cells; and (b) contacting the neural progenitor cells with an effective amount of human sonic hedgehog (SHH) protein, and FGF8A protein to stimulate the neural progenitor cells to differentiate into SN-A9 dopaminergic neurons. Optionally, the pluripotent stem cells are further contacted with a WNT1 protein.

In any of the foregoing embodiments, the pluripotent stem cells may be contacted with SHH protein, WNT1 protein, and the FGF8A protein either simultaneously with the retinoic acid or after contact with the retinoic acid. Optionally, the pluripotent stem cells are cultured in the presence of retinoic acid alone for a period of time and the SHH protein, WNT1 protein, and the FGF8A protein are applied to the cells later without removal of the retinoic acid. Combinations of the foregoing are also contemplated (e.g., in which one or two of the factors are added simultaneously with the retinoic acid and other factor(s) are added later).

In any of the foregoing embodiments, the pluripotent stem cells may be cultured either in the presence or the absence of feeder cells. In one embodiment, the pluripotent stem cells are cultured in the absence of feeder cells. In embodiments in which feeder cells are present, the feeder cells may comprise a monolayer on a solid substrate (e.g., a culture dish).

In one embodiment, the human SHH protein is activated human SHH protein. In a particular embodiment, the activated human SHH protein is C24II SHH protein. In one embodiment, the effective amount of human SHH protein is an amount sufficient to provide a final concentration in the culture media from about 100 to about 1000 ng/ml. In a particular embodiment, the effective amount of human SHH protein is an amount sufficient to provide a final concentration in the culture media of about 500 ng/ml. In yet another particular embodiment, the effective amount of WNT1 protein is an amount sufficient to provide a final concentration in the culture media of about 100 ng/ml.

In one embodiment, the WNT1 protein (e.g., human WNT1 protein) is an amount sufficient to provide a final concentration in the culture media from about 100 to about 1000 ng/ml. In a particular embodiment, the effective amount of WNT1 protein is an amount sufficient to provide a final concentration in the culture media of about 500 ng/ml. In yet another particular embodiment, the effective amount of WNT1 protein is an amount sufficient to provide a final concentration in the culture media of about 100 ng/ml.

In one embodiment, the effective amount of retinoic acid is an amount sufficient to provide a final concentration in the culture media from about $10^{-9}$ M to about $10^{-7}$ M. In a particular embodiment, the effective amount of retinoic acid is an amount sufficient to provide a final concentration in the culture media of about $10^{-8}$ M.

In one embodiment, the FGF8A is a recombinant human FGF8A protein. In one embodiment, the effective amount of human FGF8A protein is an amount sufficient to provide a final concentration in the culture media from about 10 to about 1000 ng/ml. In a particular embodiment, the effective amount of human FGF8A protein is an amount sufficient to provide a final concentration in the culture media of about 100 ng/ml.

In one aspect, the present invention provides a kit comprising the agents: (i) retinoic acid, (ii) human sonic hedgehog (SHH) protein, (iii) WNT1 protein, and (iv) FGF8A protein and instructions for contacting the agents to pluripotent stem cells in order to differentiate SN-A9 dopaminergic neurons.

In practicing the methods described herein, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzynzol.*, (Academic Press, Inc., 1984); *Gene Transfer Vectors for Mammalian Cells*, Miller & Calos, Eds. (Cold Spring Harbor Laboratory, NY, 1987); and *Meth. Enzymol* Vols. 154 and 155, Wu & Grossman, and Wu, Eds., respectively.

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent to a subject includes any route of introducing or delivering to a subject a compound to perform its intended function. Administration can be carried out by any suitable route, including orally, intranasally, parenterally (intracranially, intracerebroventricular, intravenously, intramuscularly, intraperitoneally, or subcutaneously), or topically. Administration includes self-administration and the administration by another.

As used herein, "differentiation" refers to the process whereby an unspecialized stem cell (e.g., PS cells and iPS cells) acquires phenotypic features of a specialized cell or specific cell type, e.g., a neural cell. Differentiation refers to the restriction of the potential of a cell to self-renew and is generally associated with a change in the functional capacity of the cell. Differentiation of a stem cell may be determined by methods well known in the art, including analysis for cell markers or morphological features associated with cells of a defined differentiated state.

As used herein, the term "dopaminergic neuron" refers to a specialized cell that at least partially adopts a neuronal morphology in culture (e.g., develops neurites) and expresses tyrosine hydroxylase (TH). Optionally, the dopaminergic neuron expresses one or more of neuron-specific enolase (NSE), 1-aromatic amino acid decarboxylase, vesicular monoamine transporter 2, dopamine transporter, Nurr-1, and dopamine-2 receptor ($D_2$ Receptor).

As used herein, the term "effective amount" refers to a quantity sufficient to achieve a desired physiological and/or therapeutic effect. In the context of methods for the differentiation of neural cells, an effective amount of a substance is any amount of the substance which induces pluripotent cells to differentiate into neurons. Methods of determining an "effective amount" are well known to those skilled in the art and typically involve range-finding studies to assess dose-response relationships between the substance of interest and the desired effect. Such studies may be performed in vitro or in vivo, including in a single individual by titrating the dose of the substance(s) upward until the effect is achieved.

As used herein, the term "isolated," when referring to a material, is meant a material that is partially or completely removed from the other material which naturally accompanies it. Therefore, in reference to a cell, the term "isolated" refers to a cell substantially free from other cells accompanying it in vivo. The term "isolated" in relation to nucleic acids or polypeptides means that, for example, the nucleic acids or the polypeptides are substantially free from intracellular macromolecules with which it is normally found. Any nucleic acid or polypeptide made by synthetic means (e.g., chemical synthesis and substances recombinant DNA techniques, etc.) is defined as isolated.

As used herein, the term "embryonic stem cells" (ESC) refers to cells derived from the inner cell mass of blastocysts, blastomeres, or morulae that have been serially passaged as cell lines while maintaining an undifferentiated state (e.g. express TERT, OCT4, and/or TRA antigens). The ES cells may be derived from fertilization of an egg cell with sperm or DNA, nuclear transfer, parthenogenesis, or by means to generate hES cells with hemizygosity or homozygosity in the MHC region.

As used herein, the term "pluripotent stem cell" or "PS cell" refers to a cell capable of self-replication and differentiation into cells of all three germ layers (i.e., ectoderm, mesoderm, and endoderm). Pluripotent stem cells may be, but are not limited to, ESCs and artificially-produced stem cells having characteristics of ESCs but which are not derived from an embryo (e.g., pluripotent stem cells derived from neural progenitor cells and iPS cells). In vitro self-replication, under appropriate conditions, occurs for virtually indefinite period of time and the daughter cells retain the undifferentiated (pluripotent) characteristics of the parent cells.

As used herein, the term "induced pluripotent stem cell" (iPS cell) refers to pluripotent cells derived from mesenchymal cells through the overexpression of one or more transcription factors. In one specific embodiment, iPS cells are derived from fibroblasts by the overexpression of Oct4, Sox2, c-Myc and Klf4 according to the methods described in Takahashi et al. (*Cell*, 126:663-676, 2006), for example.

Other methods for producing iPS cells are described, for example, in Takahashi et al. (*Cell*, 131:861-872, 2007) and Nakagawa et al. (*Nat. Biotechnol.*, 26:101-106, 2008). The iPS cells are capable of self-renewal and subsequent differentiation into more than one specialized cell type or cell lineage under appropriate growth conditions either in vitro or in vivo.

As used herein, "neural stem cells" refers to a subset of pluripotent cells which have partially differentiated along a neural cell pathway and express some neural markers including, for example, nestin. Neural stem cells may differentiate into neurons or glial cells (e.g., astrocytes and oligodendrocytes). Neural stem cells include neural progenitor cells and may be used interchangeably.

As used herein, "neural progenitor cells" refer to cultured cells derived from pluripotent stem cells (e.g., ES cells and iPS cells) which express FOXA2 and low levels of β-tubulin, but not tyrosine hydroxylase (i.e., having a FOXA2$^+$/β-tubulin$^{LO}$/TH$^-$ phenotype). These neural progenitor cells have the capacity to differentiate into a variety of neuronal subtypes; particularly a variety of dopaminergic neuronal subtypes, upon culturing the appropriate factors, such as those described herein.

As used herein, the term "FGF8a" refers to the splice variant of the fibroblast growth factor 8 gene product which gives rise to a protein with a predicted molecular mass of 21 kDa. The FGF8a protein is described in Matilla & Harkonnen 2007, Olsen et al., 2006, Ghosh et al 1996, Mattila et al., 2001, Valve et al., 2000. The amino acid sequence is provided at GenBank Accession No.: NP_149355.

As used herein, the term "human sonic hedgehog protein" or "(hSHH)" refers to the protein encoded by the human sonic hedgehog gene (GenBank Accession No.: NP 000184) and having the amino acid sequence proved at GenBank Accession No.: NM 000193.2, and biologically active variants and fragments thereof. The human sonic hedgehog protein is described in Carpenter et al., 1998, Ingham & McMahon 2001, Mullor et al., 2002, Perrimon 1995 and Taylor et al., 2001.

As used herein, the term "WNT1" refers to the secreted signaling protein encoded by the human WNT1 proto-oncogene and involved in regulation of cell fate and patterning during embryogenesis. WNT1 is described in, for example, Parkin et al., Activity of Wnt-1 as a transmembrane protein, Genes & Development, Vol. 7, 2181-2193, 1993.

As used herein, the term "pharmaceutically acceptable carrier" refers to a carrier that is physiologically acceptable to the treated subject while retaining the therapeutic properties of the compound with which it is administered. Exemplary pharmaceutically acceptable carriers include physiological saline and artificial cerebrospinal fluid. Other physiologically acceptable carriers and their formulations are known to one skilled in the art and described, for example, in *Remington's Pharmaceutical Sciences*, (20th edition), ed. A. Gennaro, 2000, Lippincott, Williams & Wilkins, Philadelphia, Pa.

As used herein, the terms "treating" or "treatment" or "alleviation" refers to both therapeutic treatment and prophylactic or preventative measures, wherein the object is to prevent or slow down (lessen) the targeted pathologic condition or disorder. In some embodiments, a subject is successfully "treated" for PD if, after receiving a therapeutic amount of the neural cells according to the methods described herein, the subject shows observable and/or measurable reduction in or absence of one or more signs and symptoms of PD, such as, e.g., bradykinesia, rigidity, and resting tremor. It is also to be appreciated that the various modes of treatment or prevention of medical conditions as described are intended to mean "substantial", which includes total but also less than total treatment or prevention, and wherein some biologically or medically relevant result is achieved.

As used herein, the term "subject" refers to any animal, including humans. In some embodiments, the "subject" is a human patient that is to be treated for a disease or condition.

As used herein, the term "a substantially homogenous cell population" refers to a population or sample of cells which contain a majority (i.e., >50%) of cells having the desired phenotype (i.e., trait(s) of interest). In suitable embodiments, substantially homogenous populations contain at least 60%, at least 70%, at least 80%, at least 90%, or more of the cells having the desired phenotype.

As used herein, the term "about" refers to a range of +10%, unless otherwise specified.

DETAILED DESCRIPTION

Figure 1:
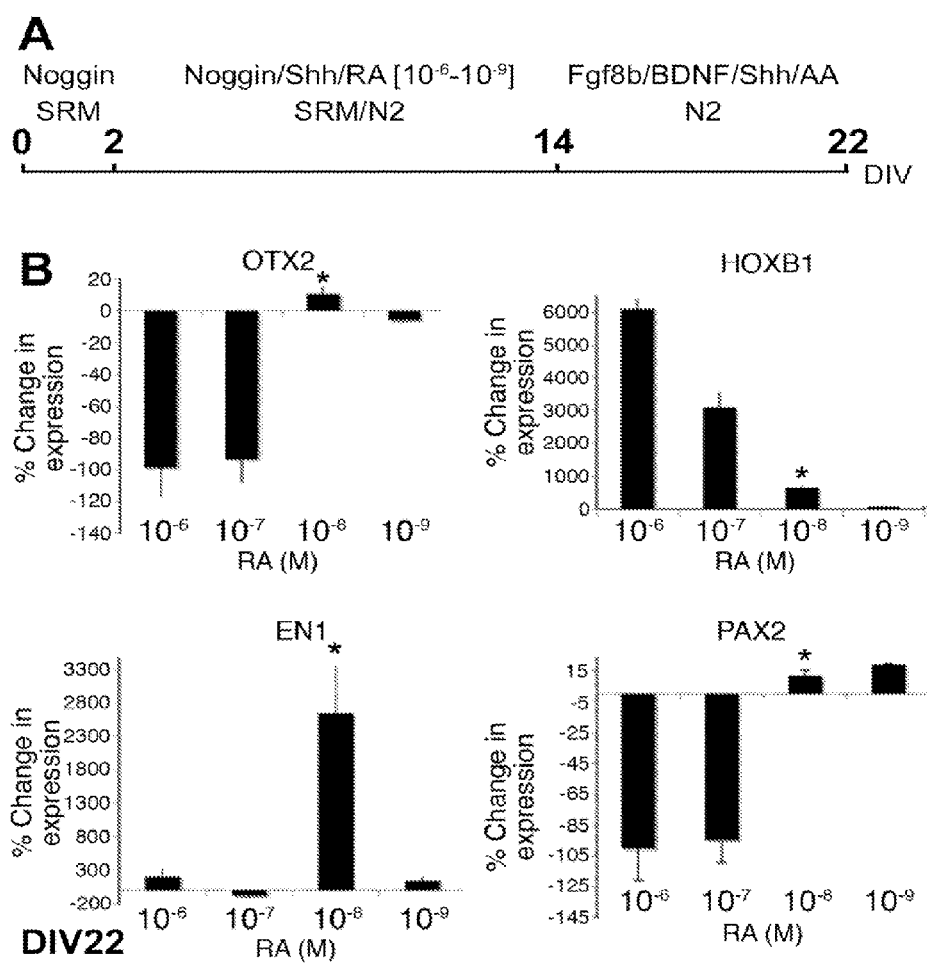
FIG. 1 presents data showing early exposure to mShh-N and $10^{-8}$ M retinoic acid promotes midbrain regionalization of human ES cell-derived neural progenitor cells. (A) Human ES cells were differentiated by 4 concentrations of RA with mouse Shh for 12 days before exposure to BDNF, ascorbic acid, mouse Shh and Fgf8b for 8 days. (B) Quantitative PCR determined that $10^{-8}$ M retinoic acid with mouse Shh induced a midbrain-like transcriptional profile by significantly increasing the levels of EN1 without changing the levels of OTX2, HOXB1 and PAX2 (* $p<0.05$ ANOVA).

The present inventions are based, in part, on the discovery that when PS cells are exposed to defined amounts of retinoic acid (RA), for specific periods of time and under specific differentiation protocols, the PS cells develop into neural progenitor cells and/or dopaminergic neurons at a higher rate than in the absence of RA. Additionally, the invention is based on the discovery that the PS cells treated with RA further establish a sizeable FOXA2$^+$ neural progenitor cell population in vitro following treatment with an activated form of human sonic hedgehog protein (SHH). Likewise, a similar FOXA2$^+$ neural progenitor cell population can be generated from PD or healthy subject-specific iPS cells using these growth conditions. The present inventors also discovered that early exposure to FGF8A, rather than Fgf8b, results in robust differentiation of the FOXA2 floor plate-like neural progenitor cells into FOXA2$^+$ DA neurons, yielding an about 100,000-fold increase in the number of FOXA2 DA neurons which resemble SN A9 and/or SN A10 dopaminergic neurons. Further, it has been discovered that human ES cell differentiation into VM DA neurons requires exogenous WNT1 signaling.

Sources of Pluripotent Stem (PS) Cells

ES cells, derived from the inner cell mass of preimplantation embryos, have been recognized as the most pluripotent stem cell population and are therefore a suitable PS cell for use with the methods and compositions of this invention. These cells are capable of unlimited proliferation ex vivo, while maintaining the capacity for differentiation into a wide variety of somatic and extra-embryonic tissues. ES cells can be male (XY) or female (XX). Stem cells can be derived from any mammal including, but not limited to, mouse, human, and primates. Following acquisition of stem cells, these cells may be used directly in the methods of the invention; for example, umbilical cord blood cells may be acquired in sufficient quantity to use directly for therapeutic purposes. Alternatively, stem cells may first be expanded in order to increase the number of available cells; see, for example, U.S. Pat. No. 6,338,942. Methods for preparing mouse, human, or primate stem cells are known in the art and are described, for example, in Nagy et al., Manipulating the Mouse Embryo: A Laboratory Manual, 3rd ed., Cold Spring Harbor Laboratory Press (2002); Thomson et al., *Science*, 282:1145-1147 (1998), Marshall et al., *Methods Mol. Biol.*, 158:11-18 (2001); Thomson et al., *Trends Biotechnol.*, 18:53-57 (2000); Jones et al., *Semin. Reprod. Med.*, 18:219-223 (2000); Voss et al., *Exp. Cell Res.*, 230:45-49 (1997); and Odorico et al., *Stem Cells*, 19:193-204 (2001).

ES cells can be directly derived from the blastocyst or any other early stage of development, or can be a "cloned" stem cell line derived from somatic nuclear transfer and other similar procedures. Briefly, in the first step, the inner cell mass of a preimplantation blastocyst is removed from the trophectoderm that surrounds it. The small plastic culture dishes used to grow the cells contain growth medium supplemented with fetal calf serum, and are sometimes coated with a "feeder" layer of nondividing cells. The feeder cells may be mouse embryonic fibroblast (MEF) cells that have been chemically inactivated so they will not divide. Additional reagents, such as the cytokine leukemia inhibitory factor (LIF), can also be added to the culture medium for mouse ES cells. Second, after several days to a week, proliferating colonies of cells are removed and dispersed into new culture dishes, each of which may or may not contain an MEF feeder layer. Under these ex vivo conditions, the ES cells aggregate to form colonies. In the third major step required to generate ES cell lines, the individual, nondifferentiating colonies are dissociated and replated into new dishes, a step called passage. This replating process establishes a "line" of ES cells. The line of cells is termed "clonal" if a single ES cell generates it. Limiting dilution methods can be used to generate a clonal ES cell line. Reagents needed for the culture of stem cells are commercially available, for example, from Invitrogen, Stem Cell Technologies, R&D Systems, and Sigma Aldrich, and are described, for example, in U.S. Patent Publication Nos. 2004/0235159 and 2005/0037492.

Induced pluripotent stem (iPS) cells are also a suitable cell for the methods of the invention. iPS cell technology can provide isogenic cells for cell therapy to limit the patient's immune response. The brain is relatively immunoprivileged but activated microglia can compromise the synaptic function of transplanted neurons (Soderstrom et al., 2008). iPS cells are a type of pluripotent stem cell artificially derived from a non-pluripotent cell, typically an adult somatic cell. Yamanaka et al. transfected mouse fibroblasts with four genes (Oct4, Sox2, c-Myc, Klf4) to obtain iPS cells in 2006. Subsequently, iPS cells were created from human adult somatic cells. (Takahashi et al. *Cell*, 131:861-872 (2007); Yu et al. *Science*, 318:1917-1920, 2007).

The iPS cell can be a mammalian cell, for example a mouse, human, rat, bovine, ovine, horse, hamster, dog, guinea pig, or non-human primate cell. For example, reprogramming of somatic cells provides an opportunity to generate patient- or disease-specific pluripotent stem cells. iPS cells are indistinguishable from ES cells in morphology, proliferation, gene expression, and teratoma formation. Human iPS cells are also expandable and indistinguishable from human embryonic stem (ES) cells in morphology and proliferation. Furthermore, these cells can differentiate into cell types of the three germ layers in vitro and in teratomas.

The mesenchymal cells useful for creating iPS cells may be obtained from any suitable source and may be any specific mesenchymal cell type. For example, if the ultimate goal is to generate therapeutic cells for transplantation into a patient, mesenchymal cells from that patient are desirably used to generate the iPS cells. Suitable mesenchymal cell types include fibroblasts (e.g., skin fibroblasts), hematopoietic cells, hepatocytes, smooth muscle cells, and endothelial cells. In suitable embodiments, the iPS cells used in the present methods are derived from a PD patient.

Methods for cell culturing, developing, and differentiating pluripotent stem cells may be carried out with reference to standard literature in the field. Suitable techniques are described by Wiles et al., *Meth. Enzymol.*, 225:900, 1993; and in *Embryonic Stem Cells* (Turksen ed., Humana Press, 2002). Established protocols for generation, passaging and preservation of rodent and human pluripotent stem cells are described by, for example, Iannaccone et al. (*Dev. Biol.*, 163:288, 1994); Matsui et al. (*Cell*, 70:841, 1992), Thomson et al., *Science*, 282:114, 1998; Shamblott et al., *Proc. Natl. Acad. Sci. USA*, 95:13726, 1998; Reubinoff et al., *Nat. Biotech.*, 18:399, 2000; U.S. Pat. Nos. 5,843,780 and 6,090,622; and PCT Publication Nos. WO 99/27076 and WO 00/27995.

Those skilled in the art will appreciate that except where explicitly required otherwise, PS cells include primary tissue and established lines that bear phenotypic characteristics of PS cells, and derivatives of such lines that still have the capacity of producing progeny of each of the three germ layers. PS cell cultures are described as "undifferentiated" or "substantially undifferentiated" when a substantial proportion of stem cells and their derivatives in the population display morphological characteristics of undifferentiated cells, clearly distinguishing them from differentiated cells of embryo or adult origin. Undifferentiated PS cells are easily recognized by those skilled in the art, and typically appear in the two dimensions of a microscopic view with high nuclear/cytoplasmic ratios and prominent nucleoli. It is understood that colonies of undifferentiated cells within the population will often be surrounded by neighboring cells that are differentiated. Nevertheless, the undifferentiated colonies persist when the population is cultured or passaged under appropriate conditions, and individual undifferentiated cells constitute a substantial proportion of the cell population. Cultures that are substantially undifferentiated contain at least 20% undifferentiated PS cells, and may contain at least 40%, 60%, or 80% undifferentiated PS cells.

Differentiation of PS Cells

In one aspect, the methods provide contacting PS cells with retinoic acid (RA), an activated form of human SHH, WNT1, and FGF8A in amounts that are sufficient to direct the fate of PS cells towards dopaminergic neurons, including those preferably having a phenotype of SN-A9 and VTA-A10 DA neurons. In some embodiments, PS cells are differentiated in the presence of about $10^{-9}$ to $10^{-7}$ M RA (e.g., about $2 \times 10^{-9}$ to about $5 \times 10^{-8}$ M or about $5 \times 10^{-9}$ to about $2 \times 10^{-8}$ M). In a particular embodiment, PS cells are differentiated in the presence of about $10^{-8}$ M RA. In some embodiments, neuroectodermal differentiation in the presence of RA was allowed to proceed from 10-18 days. In one embodiment, neuroectodermal differentiation in the presence of RA was allowed to proceed 14 days, with the media changed every 2 days. After differentiation, neuroectodermal colonies were picked and replated for differentiation toward the DA neuron phenotype.

In some embodiments, differentiation toward the DA neuron phenotype occurs by culturing the neuroectodermal colonies with an activated form of human SHH, WNT1, and FGF8A. In some embodiments, the cells are differentiated in the presence of human SHH, WNT1, and FGF8A for 18-35 days. In a particular embodiment, the cells are differentiated in the presence of human SHH, WNT1, and FGF8A for 28 days and then differentiated until Day 49 without SHH, WNT1, and FGF8A, but in the presence of one or more of (e.g., 2, 3, 4, or all 5 of) BDFN, AA, cAMP, GDNF, and TGF-β3.

In some embodiments, the human SHH is an activated form of human SHH. The mature biologically active form of SHH molecule is produced by autocatalytic cleavage of its precursor protein and corresponds to the N-terminal domain of the precursor molecule corresponding generally to residues 24-197 of the full-length human SHH protein (Pepinsky et al, 1998; Taylor et al., 2001). In one embodiment, the effective amount of human SHH protein is an amount sufficient to provide a final concentration in the culture media from about 100 to about 1000 ng/ml. In a particular embodiment, the effective amount of human SHH protein is an amount sufficient to provide a final concentration in the culture media of about 500 ng/ml. In some embodiments, neural progenitor cells are contact with an activated SHH protein. In some embodiments, a supra-potent form of the activated SHH protein may be used. Such modified activated SHH proteins include, for example, activated SHH proteins having N-terminal modifications including, for example, N-terminal acyl amides and thiazolidines, and activated SHH proteins that have been mutagenized to increase biological activity (Taylor et al., 2001). In one embodiment, the modified activated SHH is the C24II SHH which is a 20 kDa protein produced from human cells consisting of 175 amino acid residues, including an N-terminal Ile-Ile sequence substituted for the naturally occurring chemically modified Cys residue (see, Taylor et al., 2001). Other modified activated SHH proteins included, for example C24III, C24IIII, C23IIW, C24IW, C24F, C24I, C24FIF, C24W, C24I-G25I, and C24M (Taylor et al., 2001). When using supra-potent forms of the activated SHH protein, the amount used may be less than the amount of native activated SHH but sufficient to provide the same biological activity as the amounts of discussed above. Alternatively, greater amounts may be used in order to delivery higher levels of SHH biological activity to the cells.

In one embodiment, differentiation toward the DA neuron phenotype occurs by culturing the neuroectodermal colonies with FGF8A. FGF8A (fibroblast growth factor 8 A). FGF8 is a member of the fibroblast growth factor family that was originally discovered as a growth factor essential for the androgen-dependent growth of mouse mammary carcinoma cells. Splicing of mouse FGF8 mRNA generates eight secreted isoforms, designated a-h. Only FGF8a, b, e and f exist in humans. FGF8 contains a 22 amino acid (aa) signal sequence, an N-terminal domain that varies according to the isoform (20 aa for FGF8a, which is the shortest), a 125 aa FGF domain and a 37 aa proline rich C-terminal sequence. In some embodiments, the FGF8A is recombinant human FGF8A. In one embodiment, the effective amount of human FGF8A protein is an amount sufficient to provide a final concentration in the culture media from about 10 to about 1000 ng/ml human FGF8A protein. In a particular embodiment, the effective amount of human FGF8A protein is an amount sufficient to provide a final concentration in the culture media of about 100 ng/ml.

In some embodiments, differentiation toward the DA neuron phenotype occurs by culturing the neuroectodermal colonies with human WNT1 protein, either with or without Noggin, and without feeder cells (e.g., MS5 feeder cells). WNT1 has been shown in developmental studies in the embryo to be required to generate appropriately patterned VM neural progenitor cells (Muhr et al., 1999; Nordstrom et al., 2002, 2006). It is also shown herein that neuronal differentiation of FOXA2 neural progenitor cells without exogenous SHH antagonism can occur. While not wishing to be bound by any theory, this result suggests that either SHH antagonists secreted in vitro are sufficient to induce neuronal differentiation or that SHH antagonism is a modest requirement for VM DA neurogenesis in human cells. In some embodiments, the WNT1 is recombinant human WNT1. In one embodiment, the effective amount of human WNT1 protein is an amount sufficient to provide a final concentration in the culture media from about 10 to about 1000 ng/ml human WNT1 protein. In a particular embodiment, the effective amount of human WNT1 protein is an amount sufficient to provide a final concentration in the culture media of about 100 ng/ml.

Methods for the Treating of Neurodegenerative Diseases

In the central nervous system, many functionally distinct types of dopaminergic (DA) neurons are found in several brain regions. The cardinal motor symptoms of Parkinson's disease (PD) are caused by the vulnerability of a specific midbrain (SN-A9) type of DA neuron to significant degeneration. The invention provides methods for treating neurodegenerative diseases (e.g., Parkinson's Disease) in a patient by generating dopaminergic neurons, particularly dopaminergic neurons having an A9 phenotype, and transplanting these dopaminergic neurons into the brain of the patient. The dopaminergic neurons are generated from neuronal progenitor cells by contacting those cells with an effective amount of retinoic acid, human sonic hedgehog (SHH) protein, WNT1 protein, and FGF8A protein. Optionally, the neuronal progenitor cells may be generated by contacting PS cells with RA and other differentiating factors under culture conditions described herein.

Transplantation can be allogeneic (between genetically different members of the same species), autologous (transplantation of an organism's own cells or tissues), syngeneic (between genetically identical members of the same species (e.g., identical twins)), or xenogeneic (between members of different species). Ordinarily, the DA neurons would be transplanted into the substantia nigra (particularly in or adjacent of the compact region), the ventral tegmental area (VTA), the caudate, the putamen, the nucleus accumbens, the subthalamic nucleus, or any combination thereof, of the brain to replace the DA neurons whose degeneration resulted in PD. Transplantation into the substantia nigra, the caudate, or the putamen is performed because, although the cell bodies of A9 DA neurons are located in the substantia nigra, their axons extend into the forebrain structures where dopamine release occurs. In disease conditions where it is desirable to replace A10 DA neurons, the DA neurons are transplanted into the VTA, the nucleus accumbens, or both regions of the brain. In the late stages of PD, cognitive and behavioral disturbance may be generated from DA loss and synaptic dysfunction in the caudate, cerebral cortex deep layers, nucleus accumbens, and substantia nigra regions of the brain. Thus, the ventral tegmental DA neuronal phenotype of A10 would be specifically transplanted to these regions to replace lost A10 DA functions. In particular, transplantation of A10 DA neurons, or cells primed to differentiate into A10 DA neurons, to the caudate nucleus would be the most effective replacement.

Transplantation of the cells of the invention into the brain of the patient with a neurodegenerative disease results in replacement of lost, non-, or dysfunctional DA neurons. The cells are introduced into a subject with a neurodegenerative disease in an amount suitable to replace the dysfunctional DA neurons such that there is an at least partial reduction or alleviation of at least one adverse effect or symptom of the disease. The cells can be administered to a subject by any appropriate route that results in delivery of the cells to a desired location in the subject where at least a portion of the cells remain viable. It is preferred that at least about 5%, preferably at least about 10%, more preferably at least about 20%, yet more preferably at least about 30%, still more preferably at least about 40%, and most preferably at least about 50% or more of the cells remain viable after administration into a subject. The period of viability of the cells after administration to a subject can be as short as a few hours, e.g., twenty-four hours, to a few days, to as long as a few weeks to months. One transplantation method that can be used to deliver the cells to a subject is described by Bjorklund et al. (*Proc. Nat. Acad. Sci. USA*, 99:2344-2349, 2002).

To accomplish these methods of administration, the cells of the invention can be inserted into a delivery device that facilitates introduction by injection or implantation of the cells into the subject. Typically, the cells are injected into the target area as a cell suspension. Alternatively, the DA neurons can be embedded in a solid or semisolid support matrix when contained in such a delivery device.

Cell transplantation therapies typically involve the intraparenchymal (e.g., intracerebral) grafting of the replacement cell populations into the lesioned region of the nervous system, or at a site adjacent to the site of injury. Most commonly, the therapeutic cells are delivered to a specific site by stereotaxic injection. Conventional techniques for grafting are described, for example, in Bjorklund et al. (*Neural Grafting in the Mammalian CNS*, eds. Elsevier, pp. 169-178, 1985), Leksell et al. (*Acta Neurochir.*, 52:1-7, 1980) and Leksell et al. (*J. Neurosurg.*, 66:626-629, 1987). Identification and localization of the injection target regions will generally be done using a non-invasive brain imaging technique (e.g., MRI) prior to implantation (see, for example, Leksell et al., *J. Neurol. Neurosurg. Psychiatry*, 48:14-18, 1985). Briefly, administration of cells into selected regions of a patient's brain may be made by drilling a hole and piercing the dura to permit the needle of a microsyringe to be inserted. Alternatively, the cells can be injected into the brain ventricles or intrathecally into a spinal cord region. It also is possible to effect multiple grafting concurrently, at several sites, using the same cell suspension, as well as mixtures of cells. Multiple graftings are particularly useful for administration of cells to larger brain structures such as the caudate and/or putamen.

Therapeutic Compositions

Following in vitro cell culture and isolation as described herein, the cells are prepared for implantation. The cells are suspended in a physiologically compatible carrier, such as cell culture medium (e.g., Eagle's minimal essential media), phosphate buffered saline, or artificial cerebrospinal fluid (aCSF). The volume of cell suspension to be implanted will vary depending on the site of implantation, treatment goal, and cell density in the solution. For the treatment of Parkinson's Disease, about 30-100 μl of cell suspension will be administered in each intra-nigral or intra-putamenal injection and each patient may receive a single or multiple injections into each of the left and right nigral or putaminal regions.

Pharmaceutically acceptable carriers and diluents include saline, aqueous buffer solutions, solvents and/or dispersion media. The use of such carriers and diluents is well known in the art. The solution is preferably sterile and fluid. Suitably, the solution is stable under the conditions of manufacture and storage and preserved against the contaminating action of microorganisms such as bacteria and fungi through the use of, for example, parabens, chlorobutanol, phenol, ascorbic acid, or thimerosal. Solutions of the invention can be prepared by incorporating the cells as described herein in a pharmaceutically acceptable carrier or diluent and, as required, other ingredients.

In some embodiments, the cells are encapsulated within permeable membranes prior to implantation. Encapsulation provides a barrier to the host's immune system and inhibits graft rejection and inflammation. Several methods of cell encapsulation may be employed. In some instances, cells will be individually encapsulated. In other instances, many cells will be encapsulated within the same membrane. Several methods of cell encapsulation are well known in the art, such as described in European Patent Publication No. 301, 777, or U.S. Pat. Nos. 4,353,888, 4,744,933, 4,749,620, 4,814,274, 5,084,350, and 5,089,272.

In one method of cell encapsulation, the isolated cells are mixed with sodium alginate and extruded into calcium chloride so as to form gel beads or droplets. The gel beads are incubated with a high molecular weight (e.g., MW 60-500 kDa) concentration (0.03-0.1% w/v) polyamino acid (e.g., poly-L-lysine) to form a membrane. The interior of the formed capsule is re-liquefied using sodium citrate. This creates a single membrane around the cells that is highly permeable to relatively large molecules (MW~200-400 kDa), but retains the cells inside. The capsules are incubated in physiologically compatible carrier for several hours in order that the entrapped sodium alginate diffuses out and the capsules expand to an equilibrium state. The resulting alginate-depleted capsules is reacted with a low molecular weight polyamino acid which reduces the membrane permeability (MW cut-off~40-80 kDa).

Prior to introduction into a subject, the DA neurons can be modified to inhibit immunological rejection. For example, to inhibit rejection of transplanted cells and to achieve immunological non-responsiveness in a transplant recipient, the methods of the invention can include alteration of immunogenic antigens on the surface of the cells prior to introduction into the subject. This step of altering one or more immunogenic antigens on the cells can be performed alone or in combination with administering to the subject an agent that inhibits T cell activity in the subject. Alternatively, inhibition of rejection of the transplanted cells can be accomplished by administering to the subject an agent that inhibits T cell activity in the subject in the absence of prior alteration of an immunogenic antigen on the surface of the transplanted cells. An agent that inhibits T cell activity is defined as an agent which results in removal (e.g., sequestration) or destruction of T cells within a subject or inhibits T cell functions within the subject. T cells may still be present in the subject but are in a non-functional state, such that they are unable to proliferate or elicit or perform effector functions (e.g., cytokine production, cytotoxicity, etc.). The agent that inhibits T cell activity may also inhibit the activity or maturation of immature T cells (e.g., thymocytes). A suitable agent for use in inhibiting T cell activity in a recipient subject is an immunosuppressive drug that inhibits or interferes with normal immune function, e.g., cyclosporin A, FK506, or RS-61443. Additional therapeutic agents that can be administered include steroids (e.g., glucocorticoids such as prednisolone, methyl prednisolone, and dexamethasone).

EXAMPLES

The present invention is further illustrated by the following examples, which should not be construed as limiting in any way.

Example 1—Neuronal Cell Production and Related Materials and Methods

Human Pluripotent Stem Cell Culture and In Vitro Differentiation.

The human ES cell line H9 (WA-09, XX, approximate passage 35) and the human iPS cell lines A6 (XX), PDC$^{3F}$-1 (XY), PDB$^{1/ox}$_17 Puro-5 (XY), PDB$^{1/ox}$-21Puro-26 (XY) and PDB$^{1/ox}$21Puro-28 (XY) were cultured according to the guidelines established by the National Academy of Sciences. Human ES/iPS cells were propagated as described (Sonntag et al., 2007). The differentiation of human ES/iPS cells was adapted from a published protocol (Sonntag et al., 2007). Neuroectodermal differentiation was achieved using SRM for 11 days, followed by N2 medium (DMEM/F-12; Invitrogen Corporation, Carlsbad, Calif.) (N2-A; Stem Cell Technologies, Vancouver, BC, Canada) for 3 days supplemented with 600 ng/ml Noggin (R&D Systems, Inc., Minneapolis, Minn.), 100 ng/ml human WNT1 (PeproTech EC Ltd., London, UK), 100 ng/ml human FGF8A or mouse Fgf8b (R&D Systems) and all-trans retinoic acid (Sigma-Aldrich, St. Louis, Mo.) to the culture medium. Media were changed every 2 days. At day 14 of differentiation, total human neuroectodermal colonies were manually picked as described (Karki et al., 2006) and replated on polyornithine and laminin-coated culture dishes in N2 medium supplemented with growth factors.

Neural progenitor cells were differentiated toward the DA neuron phenotype with mouse sonic hedgehog (Shh-N), human activated sonic hedgehog (C24II SHH-N), mouse fibroblast growth factor 8b (FGF8b), human FGF8A (all from R&D Systems, Inc.), 20 ng/ml brain derived neurotrophic factor (BDNF) (PeproTech EC Ltd), 1 ng/ml transforming growth factor type β3 (TGF-β3) (Calbiochem, San Diego, Calif.), 10 ng/ml glial cell line-derived neurotrophic factor (GDNF), 0.5 mM dibutyryl cAMP, and 0.2 mM ascorbic acid (AA) (all from Sigma-Aldrich). After 21 days (Day 35) cells were passaged using Tryple (Invitrogen Corporation) and spun at 1,000 rpm for 5 minutes. Cells were resuspended in N2 medium and plated again at a density of approximately 1,000,000-2,000,000 cells per well (24 well plate) on polyornithine/laminin-coated dishes in the presence of BDNF, AA, SHH, and FGF8. After an additional 7 days of culture (DIV42), cells were differentiated until Day 49 without SHH and FGF8 but in the presence of BDNF, AA, cAMP, GDNF, and TGF-β3.

Lentivirus Construction and Production.

The mouse FoxA2 cDNA (obtained from Dr. Siew-Lan Ang, MRC National Institute for Medical Research, London, UK) was ligated into the lentiviral vector, pHA-GEUBC-MCS-IZsGW (Dr. Jeng-Shin Lee, Harvard Gene Therapy Initiative, Boston, Mass., USA) to generate pHAGE-UBC-mFoxA2-IZsGW. Infectious lentiviral particles were produced by 293T cells after cotransfection with the following constructs, pHDM-Hgpm2 (HIV gag-pol), pMD-tat, pRC/CMV-rev and VSV-G pseudotyped (Env). Culture medium containing virus particles was harvested and filtered through a 0.45 μm membrane. Viral particles were concentrated by ultracentrifugation and virus titers were determined by Southern blot analysis of infected human U2OS cells.

In Vitro Transduction.

The optimal multiplicity of infection (MOI) was determined empirically from a range of viral doses (MOI 0, 0.1, 1, 10) to minimize viral-induced toxicity and to maximize the transduction efficiency. Human ES cell-derived neural progenitor cells (DIV28) were briefly rinsed in phosphate-buffered saline (PBS) prior to incubation with pHAGE-UBC-mFoxA2-IZsGW or phage-UBC-MCS-IZsGW (both MOI 5) and 8 μg/ml polybrene (Sigma-Aldrich) in complete growth medium. After 12 hours, culture medium was refreshed and cells were differentiated towards the neuronal lineage for immunocytochemical or transcriptional analyses.

Quantitative Real-Time Polymerase Chain Reaction.

RNA was purified and real-time polymerase chain reaction (PCR) was performed as described (Chung C Y, 2005). For primer sequences, see Table 1. Relative gene expression differences were quantified using the $2^{-\Delta\Delta C_T}$ method (Livak and Schmittgen, 2001).

TABLE 1

Exemplary Primer Sequences

| Primer | 5'-3' sequence | SEQ ID NO. |
|---|---|---|
| EN1 f | GTG TCT GCC CAC CTC TTC TC | SEQ ID NO: 1 |
| EN1 r | GCA GTC TGT GGG GTC GTA TT | SEQ ID NO: 2 |
| OTX2 f | AGA GGA CGA CGT TCA CTC G | SEQ ID NO: 3 |

TABLE 1-continued

Exemplary Primer Sequences

| Primer | 5'-3' sequence | SEQ ID NO. |
|---|---|---|
| OTX2 r | GGG GTG CAG CAA GTC CAT AC | SEQ ID NO: 4 |
| HOXB1 f | GGT CAA TCA GAA GGA GAC GGA | SEQ ID NO: 5 |
| HOXB1 r | CGT TCC CAT AAG GGG GAT GC | SEQ ID NO: 6 |
| PAX2 f | TAT GTT CGC CTG GGA GAT TC | SEQ ID NO: 7 |
| PAX2 r | GAA AGG CTG CTG AAC TTT GG | SEQ ID NO: 8 |
| SHH f | CTC GCT GCT GGT ATG CTC G | SEQ ID NO: 9 |
| SHH r | ATC GCT CGG AGT TTC TGG AGA | SEQ ID NO: 10 |
| LMX1A f | ATG GAG GAG AAC TTC CAA AGC | SEQ ID NO: 11 |
| LMXIA r | CCC GCT CCT TCT CAT AGT | SEQ ID NO: 12 |
| b-actin f | CTC GCC TTT GCC GAT CC | SEQ ID NO: 13 |
| b-actin r | CCT TGC ACA TGC CGG AG | SEQ ID NO: 14 |

Immunocytochemistry.

Cells were fixed in 4% paraformaldehyde and analyzed by indirect immunofluorescence (Sonntag et al., 2005). Fluorescent signals were examined using an LSM510 Meta confocal microscope equipped with ultraviolet, argon, and helium-neon lasers (Carl Zeiss, Thornwood, N.Y.). The following primary antibodies were used: rabbit/sheep anti-tyrosine hydroxylase (TH) (1:300, Pel-Freez, Rogers, A K); mouse/goat anti-FoxA2/HNF3β (1:100, Santa Cruz Biotechnology, Santa Cruz, Calif.); mouse/rabbit anti-β-III-tubulin (TuJ1) (1:500, Covance, Berkeley, Calif.), mouse anti-3CB2 and mouse anti-Islet1 (1:100 and 1:50, Developmental Studies Hybridoma Bank, Iowa City, Iowa); mouse antihuman nestin, rabbit anti-SOX17 (both 1:100, Chemicon International, Temecula, Calif.); rat anti-CORIN (1:100, R & D Systems). The appropriate fluorescent-labeled secondary antibodies (1:500. Alexa Fluor goat or donkey anti-rabbit, -mouse, -rat or -goat 488, 568, 594, 647; Invitrogen Corporation) were applied for visualization, and nuclei were counterstained with Hoechst 33342 (5 µg/ml; Invitrogen Corporation). On selected coverslips, the primary antibody was omitted to verify specificity of staining.

Cell Counts.

Quantitative analysis of immunocytochemistry was performed on randomly selected confocal fields from at least two independent differentiation experiments. In each field, images of separate channels (Hoechst, 488, 568, 594) were acquired at 40× magnification on an integrated confocal microscope (LSM510/Meta, Carl Zeiss) and stereology workstation (StereoInvestigator, MBF Bioscience, Inc., Williston, Vt.), where images of cells in independent channels and merged images were counted. On average, 20-25 visual fields were acquired per 16-mm coverslip, and a total of 4,000-8,000 Hoechst cells were counted per experiment in a blinded manner by at least two investigators.

Statistical Analysis.

Data were analyzed by Tukey's ANOVA using software (JMP, SAS Institute Inc, Cary, N.C.). Statistical significance was achieved at $p<0.05$.

Example 2—Characterization of Neuronal Cells Differentiated from Pluripotent Cells Specific Midbrain Regionalization in Response to Retinoic Acid.

Coimmunoreactivity for FOXA2, tyrosine hydroxylase (TH) and β-tubulin was used to identify SN-A9/VTA-A10 DA neurons which were differentiated according to a previously published protocol (Sonntag et al., 2007). While the percentage of $TH^+/\beta$-tubulin$^+$ cells within the total cell population (Hoechst labeled) was 5.16±2.6%, surprisingly few of the $TH^+/\beta$-tubulin$^+$ cells coexpressed FOXA2 (approximately 0.00001%). Next, coimmunoreactivity for the transcription factors ISLET1 (ISL1) or PAX6, TH and β-tubulin was used to identify DA neuron subtypes that arise from the dorsal diencephalon (Marin et al., 2005; Mastick and Andrews, 2001). Cell counts revealed that 17.76±4.46% or 33.92±4% of $TH^+/\beta$-tubulin$^+$ cells coexpressed PAX6 or ISL1, respectively.

In response to these data, experiments were designed to improve the regional specification of the ES cell-derived human DA neurons in culture. A range of retinoic acid (RA) concentrations was examined for the ability to induce a midbrain-like transcriptional profile. Using human neural progenitor cells, RA concentration dependent transcriptional profiles were determined after 22 days of differentiation in the absence or presence of $10^{-6}$, $10^{-7}$, $10^{-8}$ or $10^{-9}$ M RA (FIG. 1A). Higher concentrations of RA ($10^{-6}$ M and $10^{-7}$ M) reduced OTX2 and PAX2 levels and increased HOXB1 levels relative to differentiation conditions without RA (FIG. 1B). In contrast, $10^{-8}$ M RA increased the expression levels of the midbrain transcription factor, EN1 by more than 2000-fold. In all conditions tested, expression levels of the ventral neural transcription factor, FOXA2 were consistently low. Upon neuronal differentiation of RA-treated neural progenitor cells, immunocytochemistry rarely detected DA neurons ($TH^+/\beta$-tubulin$^+$) that coexpressed FOXA2 (data not shown). Therefore, $10^{-8}$ M retinoic acid (RA) generated a human neural progenitor cell that exhibited a transcriptional profile consistent with midbrain regionalization without the appropriate ventralization signal to generate SN-A9 DA neurons.

Forced Expression of FoxA2 Induces a Ventral Midbrain Transcriptional Profile of $10^{-8}$ M RA-Treated Neurons.

Figure 2:
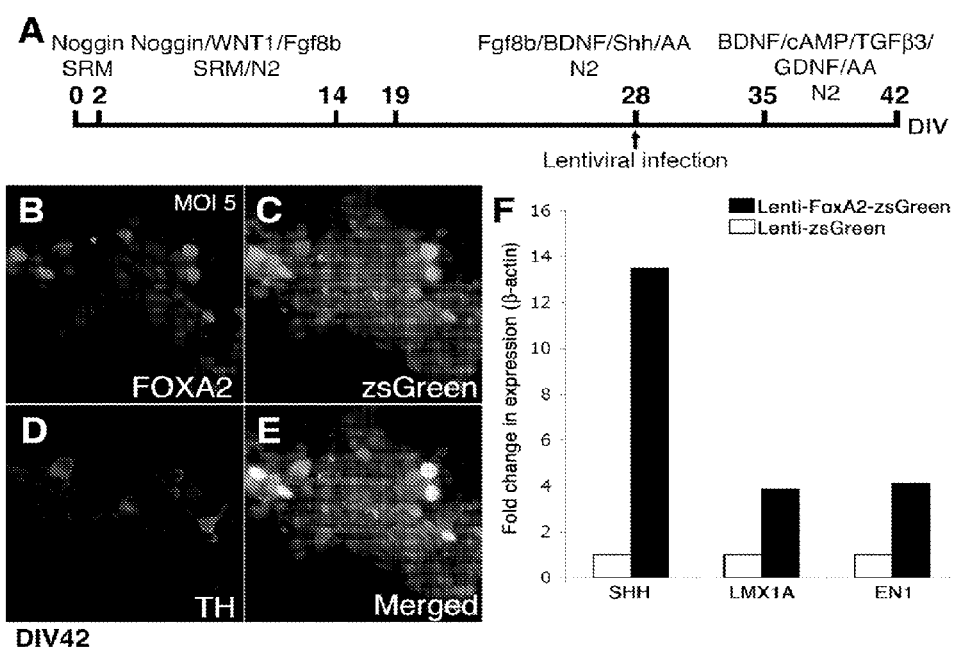
FIG. 2 presents data showing forced expression of FoxA2 promotes an A9/A10 DA neuron-like transcriptional profile in $10^{-8}$ M RA treated human ES cell-derived neurons. (A) At Day 28 of differentiation, human ES cell-derived neural progenitor cells were transduced with either a lentivirus overexpressing FoxA2-IRES-zsGreen or solely zsGreen. (B-E) Immunocytochemistry at Day 42 confirmed transgene expression of FOXA2 and zsGreen, in tyrosine hydroxylase expressing (TH) DA neurons. (F) Quantitative PCR confirmed a significant upregulation of the A9/A10 DA neuron markers SHH, LMX1A and EN1 in response to FoxA2 overexpression (* $p<0.05$ ANOVA).

Due to the lack of FOXA2 expressing human neurons in the cultures, a FOXA2 transgene was forcibly expressed in human neural progenitor cells to examine whether this gene can improve the ventral midbrain-like transcriptional profile of our cultures. Lentiviral forced expression of FoxA2 in RA-treated cells increased the levels of SN-A9/VTA-A10 DA neuron-associated transcripts, SHH, LMX1A, and EN1 (FIG. 2). Under the control of the human ubiquitin promoter, FoxA2 was overexpressed in neural progenitor cells (FIG. 2A). Forced expression of FoxA2 in RA-treated human ES cell-derived DA neurons was confirmed by immunocytochemical colocalization of FOXA2, zsGreen and TH (FIG. 2B-E). Approximately 1% of cells exhibited forced expression of FoxA2 in DA neurons. RNA isolated from parallel cultures demonstrated a significant increase in SHH, LMX1A and EN1 levels by 12, 3 and 3-fold, respectively, in response to FoxA2 forced expression (FIG. 2F). While the SN-A9/VTA-A10 transcriptional profile is improved by forced expression of FoxA2, broad changes in the transcriptional network required for functional changes in phenotype are unlikely to be achieved using a single transgene. Therefore, to avoid the use of forced expression, we investigated recombinant protein-based strategies for promoting FOXA2 expression during critical periods of in vitro differentiation.

Efficient Differentiation of Human ES and PD iPS Cells into FOXA2 Expressing Progenitor Cells Requires an Activated Form of Recombinant Human SHH.

To improve the efficiency of ventralization in the RA-treated human neural progenitor cell cultures, the role of the recombinant Shh protein used in previous differentiation protocols (Sonntag et al., 2007) was investigated. As a first step to increasing the yield of FOXA2 expressing neural progenitor cells, the concentration of the recombinant N-terminus truncated form of mouse Shh was increased from 200 ng/ml to 500 ng/ml. At 500 ng/ml, few FOXA2 expressing progenitor cells were observed (data not shown). Next, the neural progenitor cells were exposed to Shh for an additional 7 days without increasing the yield of FOXA2 expressing neural progenitor cells (data not shown).

Figure 3:
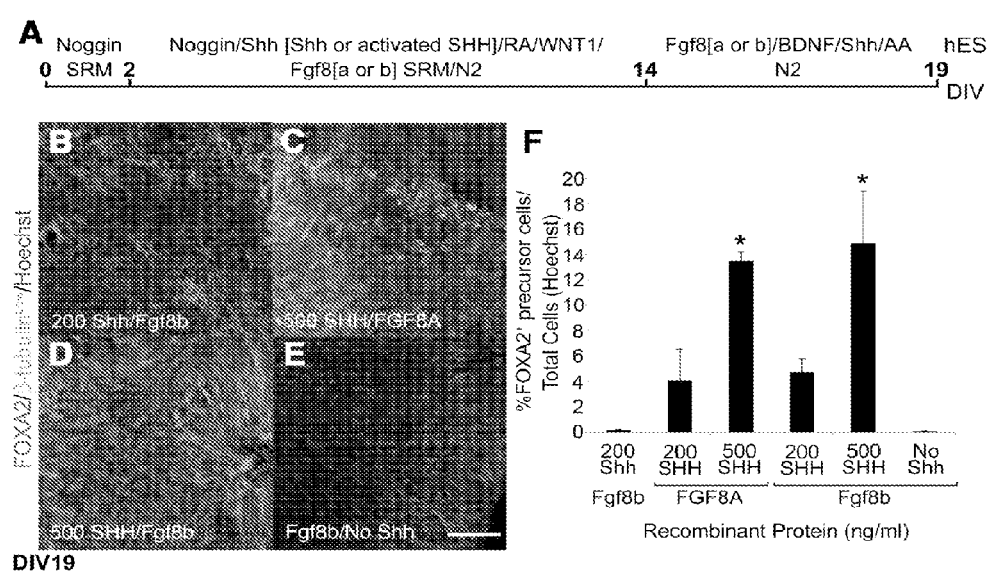
FIG. 3 presents data showing that recombinant activated human SHH promotes the dose-dependent differentiation of FOXA2 expressing neural progenitor cells from $10^{-8}$ M RA treated human ES cells. (A) Human ES cells were exposed for 12 days to an activated form of human SHH and a further 5 days to neural expansion medium. (B-E) Immunocytochemistry at DIV19 revealed few FOXA2$^+$/β-tubulin$^{Low}$ neural progenitor cells that had differentiated from human ES cells after exposure to mouse Fgf8b with (B) or without mouse Shh (E). In contrast, 500 ng/ml activated human SHH generated many FOXA2$^+$/β-tubulin$^{Low}$ neural progenitor cells in the presence of either FGF8A (C) or Fgf8b (D). (F) Cell counts revealed a significantly greater percentage of human FOXA2$^+$ neural progenitor cells after exposure to 500 ng/ml activated human SHH and either FGF8A or Fgf8b (* $p<0.05$ ANOVA). Scale bar=50 μm.
Figure 4:
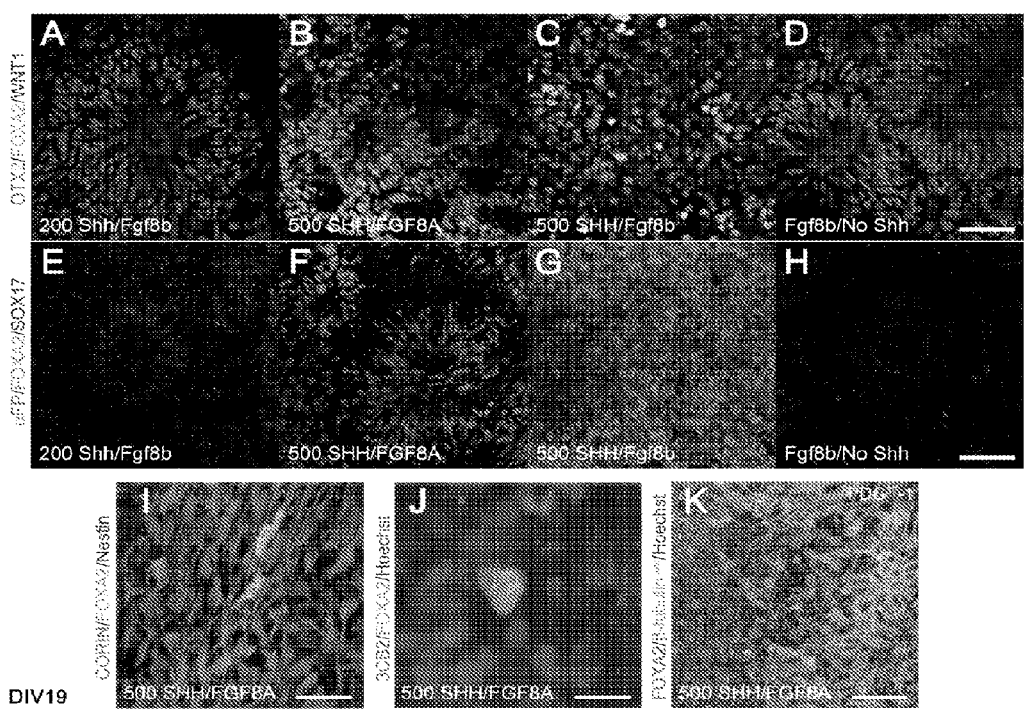
FIG. 4 presents data showing the phenotypic characterization of FOXA2 expressing neural progenitor cells from RA-treated human ES/iPS cells. (A-D) Immunocytochemistry at DIV19 revealed that human ES cell-derived neural progenitor cells formed rosette-like structures and coexpressed OTX2 and luminal WNT1 but not FOXA2, αFP or SOX17 in response to Fgf8b with (A, E) or without mouse Shh (D, H). In contrast, isolated neural rosette-like structures were observed in cultures exposed to activated human SHH and FGF8A (B, F). These rosette-like structures coexpressed OTX2, FOXA2 and WNT1 (B) but not αFP or SOX17 (F). In cultures exposed to activated human SHH and Fgf8b, very few rosette-like structures were observed and cells coexpressed FOXA2, OTX2 (C), αFP and SOX17 (G). (I) Human ES cells exposed to 500 ng/ml SHH and FGF8A or Fgf8b differentiated into FOXA2$^+$ cells that coexpressed human-specific CORIN and nestin. (J) In similar culture conditions, FOXA2$^+$ cells coexpressed 3CB2. (K) In parallel cultures, all human iPS cell lines differentiated into FOXA2$^+$/β-tubulin$^{Low}$ neural progenitor cells. Scale bar A-H, K=50 μm, I=20 μm, J=10 μm.

Next, a recombinant human SHH protein with an N-terminal mutation (Taylor et al., 2001) was substituted for the recombinant N-terminal truncated form of mouse Shh that was previously used. Importantly, the concentration of this activated form of recombinant human SHH markedly changed the yield of FOXA2 expressing progenitor cells that differentiated from RA-treated human ES and PD iPS cells. FGF8 splice variants (Olsen et al., 2006) also were explored for the ability to induce SN-A9/VTA-A10 DA neurogenesis. At DIV19 (FIG. 3A), $10^{-8}$ M RA-treated human ES cells efficiently differentiated into FOXA2$^+$/β-tubulin$^{Low}$ progenitor cells in response to 500 ng/ml of activated human SHH with either FGF8A or Fgf8b (FIG. 3C, D, F). In contrast, relatively few FOXA2$^+$ progenitor cells were observed after exposure to $10^{-8}$ M RA, Fgf8b with or without mouse Shh (FIG. 3B, E, F). Further phenotypic characterization at DIV19, revealed that the neural progenitor cells exposed to $10^{-8}$ M RA, Fgf8b with or without mouse Shh organized into rosette-like structures and expressed the forebrain and midbrain marker, OTX2 but not FOXA2 (FIG. 4A, D). The lumen of these structures was immunoreactive for WNT1, indicative of a dorsal neural phenotype (Wilkinson et al., 1987). In contrast, neural progenitor cells exposed to $10^{-8}$ M RA, activated human SHH and FGF8A organized into rosette-like structures and coexpressed OTX2, FOXA2 and WNT1, indicative of a ventral midbrain-like neural progenitor cell phenotype (FIG. 4B). Similarly, many of the neural progenitor cells exposed to $10^{-8}$ M RA, activated human SHH and Fgf8b coexpressed OTX2 and FOXA2 (FIG. 4C). However, these FOXA2 neural progenitor cells neither organized into rosette-like structures nor expressed WNT1. Due to the asynchronicity of neural induction at DIV19 and that other types of progenitor cells can express FOXA2 (Ruiz i Altaba et al., 1993), we examined the expression of the endodermal marker proteins, α-fetoprotein (αFP) and SOX17 by FOXA2 expressing human progenitor cells generated by $10^{-8}$ M RA, activated human SHH and FGF8A (FIG. 4E-H). At DIV19, neural progenitor cells exposed to $10^{-8}$ M RA, Fgf8b with or without mouse Shh did not express FOXA2, αFP or SOX17 (FIG. 4E,H). In contrast, FOXA2 expressing progenitor cells induced by $10^{-8}$ M RA, FGF8A and activated human SHH organized into rosette-like structures and did not coexpress αFP or SOX17 (FIG. 4F). However, many FOXA2 expressing progenitor cells exposed to $10^{-8}$ M RA, Fgf8b and activated human SHH coexpressed αFP and SOX17 (FIG. 4G), indicative of an endodermal lineage.

Many of the FOXA2 expressing progenitor cells generated by exposure to $10^{-8}$ M RA, FGF8A and activated human SHH coexpressed nestin (FIG. 4I), the radial glial marker 3CB2 (FIG. 4J) and NCAM (data not shown). Importantly, FOXA2 expressing neural progenitor cells expressed the floor plate marker, CORIN, only after exposure to 500 ng/ml of activated human SHH (FIG. 4I). Similarly high yields of FOXA2 expressing progenitor cells were obtained from RA-treated PD and healthy control iPS cell lines after exposure to 500 ng/ml activated human SHH and FGF8A (FIG. 4K, PDC$^{3F}$-1).

FOXA2$^+$ Neural Progenitor Cell Neurogenesis Requires Exposure to FGF8A Rather than Fgf8b During Entire Neural Induction and Expansion.

Figure 5:
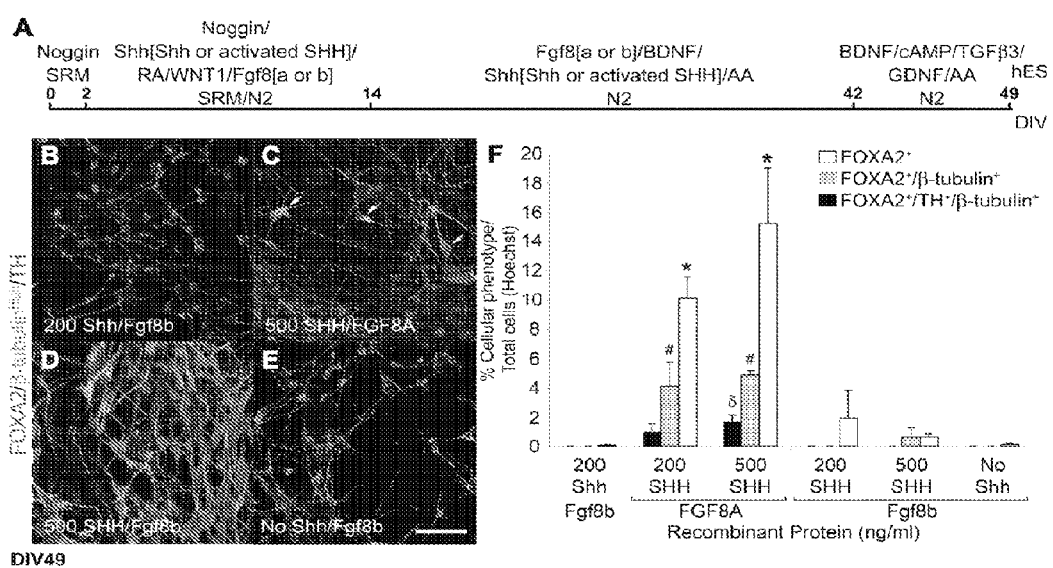
FIG. 5 presents data showing the expansion of human ES cell-derived FOXA2$^+$ neural progenitor cells by activated human SHH and human FGF8A for 28 days leads to the generation of FOXA2 expressing DA neurons. (A) Human ES cell-derived neural progenitor cells were grown in medium supplemented with Shh and FGF8 splice variants before neuronal differentiation. (B-E) Immunocytochemistry at Day 49 revealed many β-tubulin$^+$ neurons and TH$^+$ neurons but very few FOXA2$^+$ cells differentiated from human ES cells after exposure to Fgf8b with (B) or without mouse Shh (E). In contrast, 500 ng/ml activated human SHH with FGF8A (C) or Fgf8b (D) generated many FOXA2$^+$ cells. Importantly, FOXA2$^+$/β-tubulin$^{High}$/TH$^+$ neurons were only observed after exposure to FGF8A (C, arrowheads). (F) Cell counts revealed a significantly greater percentage of human FOXA2$^+$ cells (* $p<0.05$ ANOVA) and FOXA2 neurons (# $p<0.05$ ANOVA) after exposure to 200 or 500 ng/ml activated human SHH and FGF8A. A significant increase in the percentage of FOXA2$^+$ DA neurons was observed after exposure to 500 ng/ml activated human SHH and FGF8A (δ $p<0.05$ ANOVA). Scale bar=50 μm.
Figure 6:
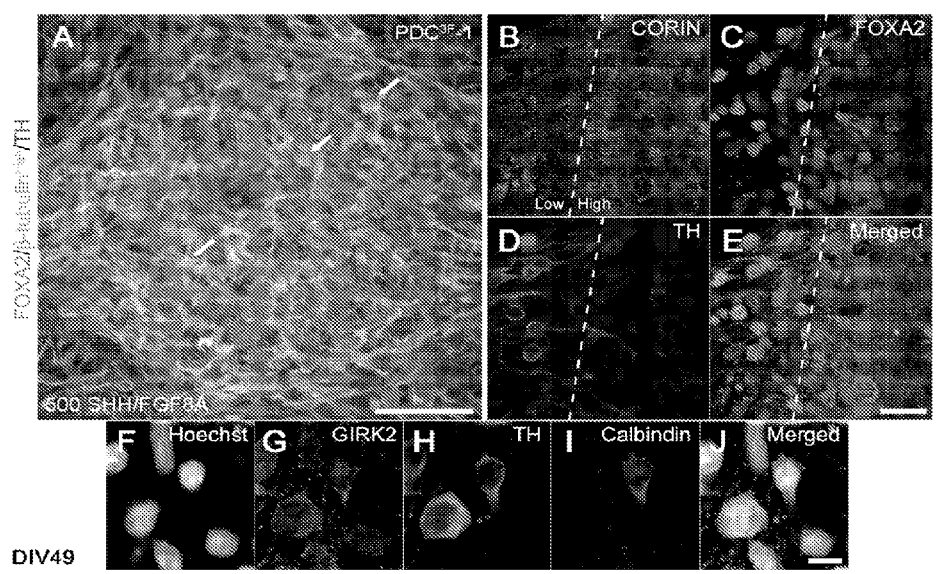
FIG. 6 presents data showing the phenotypic characterization of dopaminergic neurons generated by activated human SHH and FGF8A from RA-treated human ES/iPS cells. (A) Human PD-iPS cell lines (PDC$^{3F}$-1) were competent to generate FOXA2$^+$ dopaminergic neurons (TH; β-tubulin; arrowheads). (B-E) In human ES cell-derived cultures at DIV49, clusters of neural progenitor cells were observed. These neural progenitor cells strongly expressed CORIN (B) and FOXA2 (C), E) while adjacent cells coexpressed FOXA2 (C), TH (D) and low levels of CORIN (B, E). (F-J) In cultures differentiated with 500 ng/ml activated SHH and FGF8A, cells (F, Hoechst) expressed TH (H) and GIRK2 (G) or calbindin (I). Scale bar A=50 μm, B-E=20 μm, F-J=10 μm.

To examine the neurogenic potential of the human neural progenitor cell populations generated by these experimental conditions, we replaced Fgf8 and Shh in the culture medium with cAMP, TGFβ3 and GDNF as described (Sonntag et al., 2007). DA neurogenesis from FOXA2 expressing neural progenitor cells required extended exposure to FGF8A, while Fgf8b did not support the neuronal differentiation of FOXA2 expressing neural progenitor cells (FIG. 5). After 49 days of differentiation (FIG. 5A), few FOXA2 expressing cells were observed after differentiation with $10^{-8}$ M RA, Fgf8b with or without mouse Shh (FIG. 5B, E, F). After differentiation with $10^{-8}$ M RA, Fgf8b and activated human SHH, human ES cell-derived FOXA2 expressing cells were observed but almost none of these cells coexpressed TH and β-tubulin (FIG. 5D, F). In contrast, cultures derived from $10^{-8}$ M RA-treated human ES cells retained significantly more FOXA2 expressing cells at DIV49 when exposed to activated human SHH and FGF8A (FIG. 5C, F). Importantly, these cultures contained a significant population of cells that coexpressed FOXA2, TH and β-tubulin (FIG. 5C arrowheads, F). Similar yields of FOXA2$^+$/TH$^+$/β-tubulin$^+$ cells were obtained from PD and healthy control iPS cell lines using similar growth conditions (FIG. 6A, PDC$^{3F}$-1). At DIV49, further phenotypic characterization of the RA-treated human ES cell-derived cultures exposed to activated human SHH and FGF8A revealed FOXA2$^+$ cells that coexpressed high or low levels of the membrane protein, CORIN (FIG. 6B, C). Interestingly, these cellular clusters contained FOXA2'/CORIN$^{High}$ cells that did not express TH while many neighboring FOXA2$^+$/CORIN$^{Low}$ cells coexpressed TH (FIG. 6D, E). In similarly treated human ES cell-derived neuronal cultures, many TH expressing cells coexpressed GIRK2 or calbindin (FIG. 6F-J).

Differentiation of FOXA2 DA Neurons Requires Exposure to Recombinant WNT1 but not Noggin or MS5 Feeder Cells.

Figure 7:
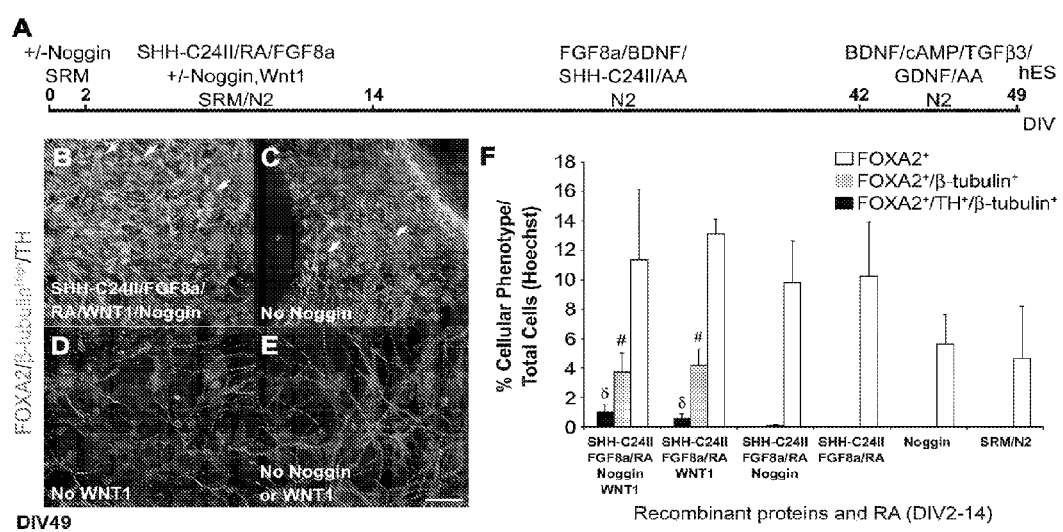
FIG. 7 presents data showing that the differentiation of human FOXA2 expressing DA neurons from ES cells requires recombinant WNT1 but not Noggin. (A) is a diagram illustrating the first 14 days of the protocol; (B)-(E) are photographs showing cells after exposure to SHH-C24II, FGF8A, and RA with (B) or without (C) Noggin; and (F) is a bar graph showing cell counts after treatment with WNT1 with or without Noggin.

To determine the requirement for recombinant WNT1 and Noggin proteins to generate FOXA2$^+$ DA neurons, human ES cells were cultured with or without WNT1 and/or Noggin, with Noggin alone or without growth factors during the first 14 days of differentiation before exposure to the previously described recombinant protein supplements, including SHH-C24II, as showing in FIG. 7(A). At DIV16, cultures grown without Noggin contained a few clusters of cells exhibiting neural differentiation. By DIV49, human ES cell-derived cultures grown with or without Noggin contained cells that coexpressed FOXA2, TH and β-tubulin, as shown in FIG. 7(B)-(C). In contrast, cultures grown without WNT1 and/or Noggin (FIGS. 7(D)-(E)), with Noggin alone, or without growth factors did not contain cells that coexpressed FOXA2, TH, and β-tubulin (FIG. 7(F)).

Figure 8:
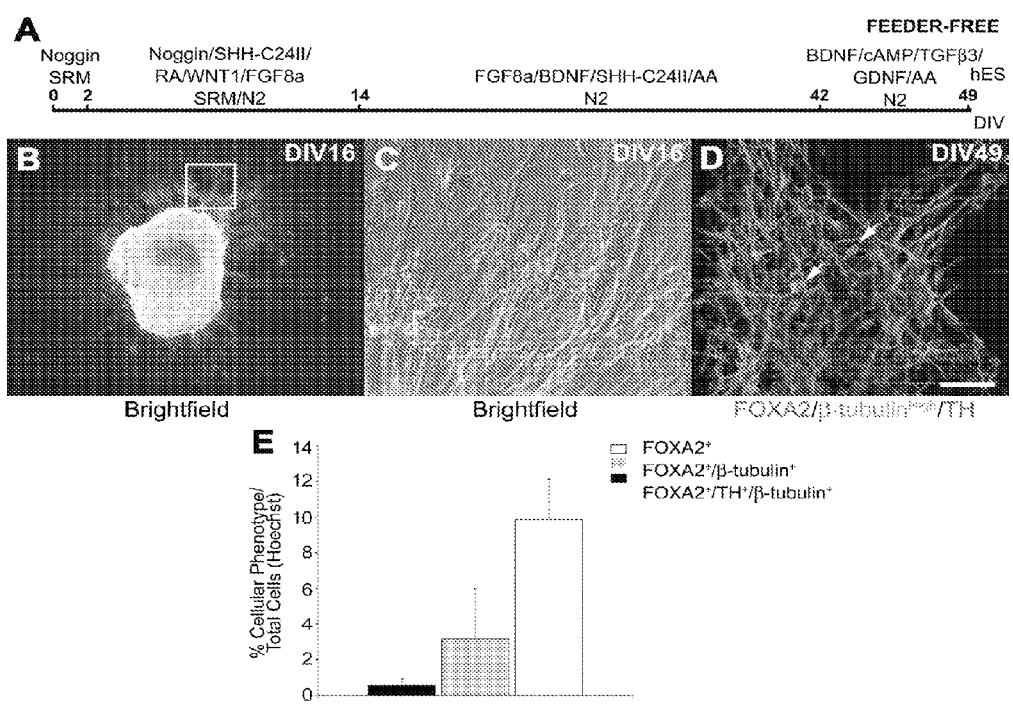
FIG. 8 presents data showing the feeder cell-free differentiation of stem cell-derived human FOXA2 expressing DA neurons. (A) is a diagram illustrating the protocol; (B)-(D) are photographs showing different magnifications of large clusters of cells that exhibited prominent radial outgrowth after the administration of the protocol.

In order to determine whether MS5-feeder cells were required for the differentiation of human FOXA2¹ DA neurons, human pluripotent stem cell lines were differentiated on gelatin-coated dishes using the previously described recombinant protein supplement, as shown in FIG. 8(A). At DIV16, brightfield microscopy revealed human cultures composed of large cellular masses that exhibited long radial outgrowth consistent with neural differentiation (FIGS. 8(B)-(C)). Upon neuronal differentiation, the dissociated cultures exhibited many cells that coexpressed TH, β-tubulin, and FOXA2 (FIGS. 8(D)-(E)).

CONCLUSION

A combination of RA, an activated form of human SHH and exposure to FGF8A was sufficient to direct the fate of human ES/iPS cells towards SN-A9 and VTA-A10 DA neurons. The cellular yield of SN-A9/VTA-A10 DA neurons was improved by targeting both early posteriorizing and ventralizing neural patterning pathways. Although isolated non-neural cell types may remain in these cultures, enriched populations (even purified populations) of SN-A9/VTA-A10 DA neurons may be separated from these mixed cultures using techniques such as flow cytometry.

REFERENCES

Ang, S. L., 2006. Transcriptional control of midbrain dopaminergic neuron development. *Development*, 133:3499-3506.

Cai, J., Donaldson, A., Yang, M., German, M. S., Enikolopov, G., Iacovitti, L., 2009. The role of Lmx1a in the differentiation of human embryonic stem cells into midbrain dopamine neurons in culture and after transplantation into a Parkinson's disease model. *Stem Cells*, 27:220-229.

Chiang, C., Litingtung, Y., Lee, E., Young, K. E., Corden, J. L., Westphal, H., Beachy, P. A., 1996. Cyclopia and defective axial patterning in mice lacking Sonic hedgehog gene function. *Nature*, 383:407-413.

Cho, M. S., Lee, Y. E., Kim, J. Y., Chung, S., Cho, Y. H., Kim, D. S., Kang, S. M., Lee, H., Kim, M. H., Kim, J. H., Leem, J. W., Oh, S. K., Choi, Y. M., Hwang, D. Y., Chang, J. W., Kim, D. W., 2008. Highly efficient and large-*scale generation of functional dopamine neurons from human embryonic stem cells. Proc Natl Acad Sci USA*, 105:3392-3397.

Chung, C. Y., Seo, H., Sonntag, K. C., Brooks, A., Lin, L., Isacson, O., 2005. Cell typespecific gene expression of midbrain dopaminergic neurons reveals molecules involved in their vulnerability and protection. *Hum Mol Genet*, 14:1709-1725.

Chung C Y, S. H., Sonntag K C, Brooks A, Lin L, Isacson O., 2005. Cell type specific gene expression of midbrain dopaminergic neurons reveals molecules involved in their vulnerability and protection. *Human Molecular Genetics*, 14(13):1709-25.

Chung, S., Leung, A., Han, B. S., Chang, M. Y., Moon, J. I., Kim, C. H., Hong, S., Pruszak, J., Isacson, O., Kim, K. S., 2009. Wnt1-lmx1a forms a novel autoregulatory loop and controls midbrain dopaminergic differentiation synergistically with the SHH-FoxA2 pathway. *Cell Stein Cell*, 5:646-658.

Damier, P., Hirsch, E. G., Agid, Y., Graybiel, A. M., 1999. The substantia nigra of the human brain. II. Patterns of loss of dopamine-containing neurons in Parkinson's disease. *Brain*, 122:1437-1448.

Earley, C. J., Allen, R. P., Connor, J. R., Ferrucci, L., Troncoso, J., 2009. The dopaminergic neurons of the A11 system in RLS autopsy brains appear normal. *Sleep Med*, 10:1155-1157.

Epstein, D. J., McMahon, A. P., Joyner, A. L., 1999. Regionalization of Sonic hedgehog transcription along the anteroposterior axis of the mouse central nervous system is regulated by Hnf3-dependent and -independent mechanisms. *Development*, 126:281-292.

Erceg, S., Ronaghi, M., Stojkovic, M., 2009. Human embryonic stem cell differentiation toward regional specific neural precursors. *Stem Cells*, 27:78-87.

Ferri, A. L., Lin, W., Mavromatakis, Y. E., Wang, J. C., Sasaki, H., Whitsett, J. A., Ang, S. L., 2007. Foxa1 and Foxa2 regulate multiple phases of midbrain dopaminergic neuron development in a dosage-dependent manner. *Development*, 134:2761-2769.

Gaspard, N., Bouschet, T., Hourez, R., Dimidschstein, J., Naeije, G., van den Ameele, J., Espuny-Camacho, I., Herpoel, A., Passante, L., Schiffmann, S. N., Gaillard, A., Vanderhaeghen, P., 2008. An intrinsic mechanism of corticogenesis from embryonic stem cells. *Nature*, 455:351-357.

German, D. C., Manaye, K., Smith, W. K., Woodward, D. J., Saper, C. B., 1989. Midbrain dopaminergic cell loss in Parkinson's disease: computer visualization. *Ann Neurol*, 26:507-514.

German, D. C., Manaye, K. F., Sonsalla, P. K., Brooks, B. A., 1992. Midbrain dopaminergic cell loss in Parkinson's disease and MPTP-induced parkinsonism: sparing of calbindin-D28k-containing cells. *Ann. N.Y. Acad. Sci.*, 648:42-62.

Hirsch, E., Graybiel, A. M., Agid, Y. A., 1988. Melanized dopaminergic neurons are differentially susceptible to degeneration in Parkinson's disease. *Nature*, 334:345-348.

Hu, B. Y., Zhang, S. C., 2009. Differentiation of spinal motor neurons from pluripotent human stem cells. *Nat Protoc*, 4:1295-1304.

Hynes, M., Porter, J. A., Chiang, C., Chang, D., Tessier-Lavigne, M., Beachy, P. A., Rosenthal, A., 1995. Induction of midbrain dopaminergic neurons by Sonic hedgehog. *Neuron*, 15:35-44.

Isacson, O., Bjorklund, L. M., Schumacher, J. M., 2003. Towards full restoration of synaptic and terminal function of the dopaminergic system in Parkinson's disease from regeneration and neuronal replacement by stem cells. *Annals of Neurology*, 53:135-148.

Joksimovic, M., Anderegg, A., Roy, A., Campochiaro, L., Yun, B., Kittappa, R., McKay, R., Awatramani, R., 2009a. Spatiotemporally separable Shh domains in the midbrain define distinct dopaminergic progenitor pools. *Proc Natl Acad Sci USA*, 106:19185-19190.

Joksimovic, M., Yun, B. A., Kittappa, R., Anderegg, A. M., Chang, W. W., Taketo, M. M., McKay, R. D., Awatramani, R. B., 2009b. Wnt antagonism of Shh facilitates midbrain floor plate neurogenesis. *Nature Neuroscience*, 12:125-131.

Jonsson, M. E., Ono, Y., Bjorklund, A., Thompson, L. H., 2009. Identification of transplantable dopamine neuron precursors at different stages of midbrain neurogenesis. *Exp Neurol*, 219:341-354.

Karki, S., Pruszak, J., Isacson, O., Sonntag, K. C., 2006. ES cell-derived neuroepithelial cell cultures. *J Vis Exp*, 118.

Kittappa, R., Chang, W. W., Awatramani, R. B., McKay, R. D., 2007. The foxa2 gene controls the birth and spontaneous degeneration of dopamine neurons in old age. *PLoS Biol*, 5:e325.

Lee, H. S., Bae, E. J., Yi, S. H., Shim, J. W., Jo, A. Y., Kang, J. S., Yoon, E. H., Rhee, Y. H., Park, C. H., Koh, H. C., Kim, H. J., Choi, H. S., Han, J. W., Lee, Y. S., Kim, J., Li, J. Y., Brundin, P., Lee, S. H., Foxa2 and Nurr1 Synergistically Yield A9 Nigral Dopamine Neurons Exhibiting Improved Differentiation, Function and Cell Survival. *Stem Cells*.

Lee, S. M., Danielian, P. S., Fritzsch, B., McMahon, A. P., 1997. Evidence that FGF8 signalling from the midbrain-hindbrain junction regulates growth and polarity in the developing midbrain. *Development*, 124:959-969.

Li, X. J., Zhang, X., Johnson, M. A., Wang, Z. B., Lavaute, T., Zhang, S. C., 2009. Coordination of sonic hedgehog and Wnt signaling determines ventral and dorsal telencephalic neuron types from human embryonic stem cells. *Development*, 136:4055-4063.

Lin, W., Metzakopian, E., Mavromatakis, Y. E., Gao, N., Balaskas, N., Sasaki, H., Briscoe, J., Whitsett, J. A., Goulding, M., Kaestner, K. H., Ang, S. L., 2009. Foxa1 and Foxa2 function both upstream of and cooperatively with Lmx1a and Lmx1b in a feedforward loop promoting mesodiencephalic dopaminergic neuron development. *Dev Biol*, 333:386-396.

Liu, A., Losos, K., Joyner, A. L., 1999. FGF8 can activate Gbx2 and transform regions of the rostral mouse brain into a hindbrain fate. *Development*, 126:4827-4838.

Livak, K. J., Schmittgen, T. D., 2001. Analysis of relative gene expression data using realtime quantitative PCR and the 2(-Delta Delta C(T)) Method. *Methods*, 25:402-408.

Maden, M., 2007. Retinoic acid in the development, regeneration and maintenance of the nervous system. *Nat Rev Neurosci*, 8:755-765.

Marin, F., Herrero, M. T., Vyas, S., Puelles, L., 2005. Ontogeny of tyrosine hydroxylase mRNA expression in mid- and forebrain: neuromeric pattern and novel positive regions. *Dev Dyn*, 234:709-717.

Mastick, G. S., Andrews, G. L., 2001. Pax6 regulates the identity of embryonic diencephalic neurons. *Mol Cell Neurosci*, 17:190-207.

Matsuda, W., Furuta, T., Nakamura, K. C., Hioki, H., Fujiyama, F., Arai, R., Kaneko, T., 2009. Single nigrostriatal dopaminergic neurons form widely spread and highly dense axonal arborizations in the neostriatum. *J Neurosci*, 29:444-453.

McRitchie, D. A., Hardman, C. D., Halliday, G. M., 1996. Cytoarchitectural distribution of calcium binding proteins in midbrain dopaminergic regions of rats and humans. *J Comp Neurol*, 364:121-150.

Mendez, T., Sanchez-Pernaute, R., Cooper, O., Vinuela, A., Ferrari, D., Bjorklund, L., Dagher, A., Isacson, O., 2005. Cell type analysis of functional fetal dopamine cell suspension transplants in the striatum and substantia nigra of patients with Parkinson's disease. *Brain*, 128:1498-1510.

Neuhoff, H., Neu, A., Liss, B., Roeper, J., 2002. I(h) channels contribute to the different functional properties of identified dopaminergic subpopulations in the midbrain. *J Neurosci*, 22:1290-1302.

Okada, Y., Shimazaki, T., Sobue, G., Okano, H., 2004. Retinoic-acid-concentration dependent acquisition of neural cell identity during in vitro differentiation of mouse embryonic stem cells. *Dev Biol*, 275:124-142.

Olsen, S. K., Li, J. Y., Bromleigh, C., Eliseenkova, A. V., Ibrahimi, O. A., Lao, Z., Zhang, F., Linhardt, R. J., Joyner, A. L., Mohammadi, M., 2006. Structural basis by which alternative splicing modulates the organizer activity of FGF8 in the brain. *Genes Dev*, 20:185-198.

Ono, Y., Nakatani, T., Sakamoto, Y., Mizuhara, E., Minaki, Y., Kumai, M., Hamaguchi, A., Nishimura, M., Inoue, Y., Hayashi, H., Takahashi, J., Imai, T., 2007. Differences in neurogenic potential in floor plate cells along an antero-posterior location: midbrain dopaminergic neurons originate from mesencephalic floor plate cells. *Development*, 134:3213-3225.

Pepinsky et al., 1998. Identification of a palmitic acid-modified form of human sonic hedgehog. *J. Biol. Chem.*, 273:14037-14045.

Perrier, A. L., Tabar, V., Barberi, T., Rubio, M. E., Bruses, J., Topf, N., Harrison, N. L., Studer, L., 2004. Derivation of midbrain dopamine neurons from human embryonic stem cells. *Proc Natl Acad Sci USA*, 101:12543-12548.

Pfaff, S. L., 2008. Developmental neuroscience: Hox and Fox. *Nature*, 455:295-297.

Pruszak, J., Ludwig, W., Blak, A., Alavian, K., Isacson, O., 2009. CD15, CD24 and CD29 Define a Surface Biomarker Code for Neural Lineage Differentiation of Stem Cells. *Stem Cells*.

Pruszak, J., Sonntag, K. C., Aung, M. H., Sanchez-Pernaute, R., Isacson, O., 2007. Markers and methods for cell sorting of human embryonic stem cellderived neural cell populations. *Stem Cells*, 25:2257-2268.

Qu, S., Ondo, W. G., Zhang, X., Xie, W. J., Pan, T. H., Le, W. D., 2006. Projections of diencephalic dopamine neurons into the spinal cord in mice. *Exp Brain Res*, 168: 152-156.

Roelink, H., Porter, J. A., Chiang, C., Tanabe, Y., Chang, D. T., Beachy, P. A., Jessell, T. M., 1995. Floor plate and motor neuron induction by different concentrations of the amino-terminal cleavage product of sonic hedgehog autoproteolysis. *Cell*, 81:445-455.

Roy, N. S., Cleren, C., Singh, S. K., Yang, L., Beal, M. F., Goldman, S. A., 2006. Functional engraftment of human ES cell-derived dopaminergic neurons enriched by coculture with telomerase-immortalized midbrain astrocytes. *Nature Medicine*, 12:1259-1268.

Ruiz i Altaba, A., Prezioso, V. R., Darnell, J. E., Jessell, T. M., 1993. Sequential expression of HNF-3 beta and HNF-3 alpha by embryonic organizing centers: the dorsal lip/node, notochord and floor plate. *Mech Dev*, 44:91-108.

Sasaki, H., Hui, C., Nakafuku, M., Kondoh, H., 1997. A binding site for Gli proteins is essential for HNF-3beta floor plate enhancer activity in transgenics and can respond to Shh in vitro. *Development*, 124:1313-1322.

Soderstrom, K. E., Meredith, G., Freeman, T. B., McGuire, S. O., Collier, T. J., Sortwell, C. E., Wu, Q., Steece-Collier, K., 2008. The synaptic impact of the host immune response in a parkinsonian allograft rat model: Influence on graft-derived aberrant behaviors. *Neurobiol Dis*, 32:229-242.

Soldner, F., Hockemeyer, D., Beard, C., Gao, Q., Bell, G. W., Cook, E. G., Hargus, G., Blak, A., Cooper, O., Mitalipova, M., Isacson, O., Jaenisch, R., 2009. Parkinson's disease patient-derived induced pluripotent stem cells free of viral reprogramming factors. *Cell*, 136:964-977.

Sonntag, K. C., Pruszak, J., Yoshizaki, T., van Arensbergen, J., Sanchez-Pernaute, R., Isacson, O., 2007. Enhanced yield of neuroepithelial precursors and midbrain-like dopaminergic neurons from human embryonic stem cells using the bone morphogenic protein antagonist noggin. *Stem Cells*, 25:411-418.

Sonntag, K. C., Simantov, R., Bjorklund, L., Cooper, O., Pruszak, J., Kowalke, F., Gilmartin, J., Ding, J., Hu, Y. P., Shen, M. M., Isacson, O., 2005. Context-dependent neuronal differentiation and germ layer induction of Smad4−/− and Cripto−/− embryonic stem cells. *Mol Cell Neurosci*, 28:417-429.

Sonntag, K. C., Simantov, R., Kim, K. S., Isacson, O., 2004. Temporally induced Nurr1 can induce a non-neuronal dopaminergic cell type in embryonic stem cell differentiation. *Eur J Neurosci*, 19:1141-1152.

Taylor, F. R., Wen, D., Garber, E. A., Carmillo, A. N., Baker, D. P., Arduini, R. M., Williams, K. P., Weinreb, P. H., Rayhorn, P., Hronowski, X., Whitty, A., Day, E. S., Boriack-Sjodin, A., Shapiro, R. I., Galdes, A., Pepinsky, R. B., 2001. Enhanced potency of human Sonic hedgehog by hydrophobic modification. *Biochemistry*, 40:4359-4371.

Wilkinson, D. G., Bailes, J. A., McMahon, A. P., 1987. Expression of the protooncogene int-1 is restricted to specific neural cells in the developing mouse embryo. *Cell*, 50:79-88.

Wolfart, J., Neuhoff, H., Franz, O., Roeper, J., 2001. Differential expression of the small-conductance, calcium-activated potassium channel SK3 is critical for pacemaker control in dopaminergic aminergic midbrain neurons. *J Neurosci*, 21:3443-3456.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method for generating human dopaminergic neurons that coexpress β-tubulin, FOXA2, and tyrosine hydroxlyase (TH), the method comprising:
   (a) contacting human pluripotent stem cells with about $10^{-9}$ M to about $10^{-7}$ M retinoic acid for at least three days, further contacting them with a WNT1 protein and optionally with 100-1000 ng/mL FGF8A for the at least three days to generate specified neuroectodermal cells;
   (b) contacting the neuroectodermal cells produced in step (a) 100-1000 ng/mL human sonic hedgehog (SHH) protein and 10-1000 ng/mL FGF8A protein for 18-35 days to generate FOXA2 expressing dopaminergic progenitor cells and
   (c) culturing the FOXA2 expressing dopaminergic progenitor cells of step (b) in a medium that lacks SHH and FGF8A but comprises brain-derived neurotrophic factor (BDNF), ascorbic acid, cyclic AMP (cAMP), glial-derived neurotrophic factor (GDNF) and transforming growth factor beta 3 (TGF-β3) for at least seven days, thereby generating human dopaminergic neurons expressing β-tubulin, FOXA2, and TH that are capable of structurally and functionally integrating into the host following transplantation.

2. The method of claim 1, wherein the pluripotent stem cells are not co-cultured with feeder cells.

3. The method of claim 1, wherein the pluripotent stem cells are induced pluripotent stem cells.

4. The method of claim 1, wherein the human SHH protein is activated human SHH protein.

5. The method of claim 1, wherein the pluripotent stem cells are contacted with retinoic acid for about 14-49 days.

6. The method of claim 1, wherein the pluripotent stem cells are contacted with retinoic acid prior to being contacted with human SHH protein, WNT1 protein and/or FGF8A.

7. A method for increasing the number of FOXA2 expressing dopaminergic cells in a culture, the method comprising:
   (a) contacting human pluripotent stem cells with about $10^{-9}$ M to about $10^{-7}$ M retinoic acid for about 14 to 49 days to generate specified neuroectodermal cells;
   (b) contacting the specified neuroectodermal cells with 100-1000 ng/mL human sonic hedgehog (SHUT) protein and 10-1000 ng/mL FGF8A protein to generate FOXA2 expressing dopaminergic progenitor cells, and
   (c) culturing the FOXA2 expressing dopaminergic progenitor cells with a cell culture medium comprising brain-derived neurotrophic factor (BDNF), ascorbic acid, cyclic AMP (cAMP), glial-derived neurotrophic factor (GDNF) and transforming growth factor beta 3 (TGF-β3) but lacking SHUT and FGF8A for at least 7 days to generate human FOXA2 expressing dopaminergic neurons that are capable of structurally and functionally integrating into the host following transplantation,
   wherein the number of human FOXA2 expressing dopaminergic cells in the culture is higher than the number of human FOXA2 expressing dopaminergic cells in a culture that has not been treated with FGF8A.

8. The method of claim 7, wherein the human SHH protein is activated human SHH protein.

* * * * *